(12) United States Patent
Naqvi et al.

(10) Patent No.: US 9,116,144 B2
(45) Date of Patent: Aug. 25, 2015

(54) METHODS FOR PREPARING THERMALLY RESPONSIVE CELL CULTURE SURFACES

(71) Applicant: Innovative Surface Technologies, Inc., St. Paul, MN (US)

(72) Inventors: Tahmina Naqvi, Blaine, MN (US); Jie Wen, St. Johns, FL (US); Patrick Guire, Hopkins, MN (US)

(73) Assignee: INNOVATIVE SURFACE TECHNOLOGIES, INC., St. Paul, MN (US)

( * ) Notice: Subject to any disclaimer, the term of this patent is extended or adjusted under 35 U.S.C. 154(b) by 130 days.

(21) Appl. No.: 13/710,390

(22) Filed: Dec. 10, 2012

(65) Prior Publication Data

US 2013/0171331 A1 Jul. 4, 2013

Related U.S. Application Data

(62) Division of application No. 12/666,168, filed as application No. PCT/US2008/067708 on Jun. 20, 2008, now abandoned.

(60) Provisional application No. 60/945,801, filed on Jun. 22, 2007.

(51) Int. Cl.

| | |
|---|---|
| G01N 33/48 | (2006.01) |
| A61L 27/16 | (2006.01) |
| A61L 27/34 | (2006.01) |
| A61L 27/50 | (2006.01) |
| A61L 27/54 | (2006.01) |
| A61L 29/04 | (2006.01) |
| A61L 29/08 | (2006.01) |
| A61L 29/14 | (2006.01) |
| A61L 29/16 | (2006.01) |
| A61L 31/04 | (2006.01) |
| A61L 31/10 | (2006.01) |
| A61L 31/14 | (2006.01) |
| A61L 31/16 | (2006.01) |
| C12M 1/00 | (2006.01) |
| D01D 5/00 | (2006.01) |
| D01F 1/10 | (2006.01) |
| D01F 6/22 | (2006.01) |
| D01F 6/26 | (2006.01) |
| D01F 6/62 | (2006.01) |
| D06M 15/285 | (2006.01) |

(52) U.S. Cl.
CPC .............. *G01N 33/48* (2013.01); *A61L 27/16* (2013.01); *A61L 27/34* (2013.01); *A61L 27/50* (2013.01); *A61L 27/54* (2013.01); *A61L 29/041* (2013.01); *A61L 29/085* (2013.01); *A61L 29/14* (2013.01); *A61L 29/16* (2013.01); *A61L 31/048* (2013.01); *A61L 31/10* (2013.01); *A61L 31/14* (2013.01); *A61L 31/16* (2013.01); *C12M 23/20* (2013.01); *D01D 5/0007* (2013.01); *D01F 1/10* (2013.01); *D01F 6/22* (2013.01); *D01F 6/26* (2013.01); *D01F 6/625* (2013.01); *D06M 15/285* (2013.01); *A61L 2300/00* (2013.01); *D06M 2400/01* (2013.01)

(58) Field of Classification Search
USPC ......................................... 435/396, 398, 399
See application file for complete search history.

(56) References Cited

U.S. PATENT DOCUMENTS

| | | | |
|---|---|---|---|
| 3,580,927 | A | 5/1971 | Wear |
| 3,959,078 | A | 5/1976 | Guire |
| 4,043,331 | A | 8/1977 | Martin et al. |
| 4,266,055 | A | 5/1981 | Inoue et al. |
| 4,605,413 | A | 8/1986 | Urry et al. |
| 4,722,906 | A | 2/1988 | Guire |
| 4,973,493 | A | 11/1990 | Guire |
| 5,002,582 | A | 3/1991 | Guire et al. |
| 5,202,361 | A | 4/1993 | Zimmerman et al. |
| 5,258,041 | A | 11/1993 | Guire et al. |
| 5,284,766 | A | 2/1994 | Okano et al. |
| 5,331,027 | A | 7/1994 | Whitbourne |
| 5,414,075 | A | 5/1995 | Swan et al. |
| 5,522,879 | A | 6/1996 | Scopelianos |
| 5,563,056 | A | 10/1996 | Swan et al. |

(Continued)

FOREIGN PATENT DOCUMENTS

| | | |
|---|---|---|
| EP | 1857126 A1 | 11/2007 |
| JP | 57042742 | 3/1982 |

(Continued)

OTHER PUBLICATIONS

International Search Report for corresponding International Patent Application No. PCT/US2008/067708, completed Apr. 29, 2009, 8 pages.

(Continued)

*Primary Examiner* — Jim Ketter
*Assistant Examiner* — Antonio Galisteo Gonzalez
(74) *Attorney, Agent, or Firm* — Weaver Legal and Consulting LLC; Karrie G. Weaver

(57) ABSTRACT

A stimuli responsive nanofiber that includes a stimuli responsive polymer, such as a thermally responsive polymer, and a cross-linking agent having at least two latent reactive activatable groups. The nanofiber may also include a biologically active material or a functional polymer. The stimuli responsive nanofiber can be used to modify the surface of a substrate. When the nanofiber includes a thermally responsive polymer, the physical properties of the surface can be controlled by controlling the temperature of the system, thus controlling the ability of the surface to bind to a biologically active material of interest.

8 Claims, 6 Drawing Sheets

(56) References Cited

U.S. PATENT DOCUMENTS

| | | | |
|---|---|---|---|
| 5,637,460 | A | 6/1997 | Swan et al. |
| 5,714,360 | A | 2/1998 | Swan et al. |
| 5,942,555 | A | 8/1999 | Swanson et al. |
| 5,997,961 | A | 12/1999 | Feng et al. |
| 6,077,698 | A | 6/2000 | Swan et al. |
| 6,096,369 | A | 8/2000 | Anders et al. |
| 6,278,018 | B1 | 8/2001 | Swan et al. |
| 6,391,948 | B1 | 5/2002 | Clark et al. |
| 6,395,429 | B1 | 5/2002 | Kang et al. |
| 7,348,055 | B2 | 3/2008 | Chappa et al. |
| 2002/0004140 | A1 | 1/2002 | Swan et al. |
| 2003/0036196 | A1 | 2/2003 | Okano et al. |
| 2003/0165613 | A1 | 9/2003 | Chappa et al. |
| 2005/0095695 | A1 | 5/2005 | Schindler et al. |
| 2006/0030669 | A1 | 2/2006 | Taton et al. |
| 2007/0003707 | A1 | 1/2007 | Guire et al. |
| 2007/0082393 | A1 | 4/2007 | Lodhi et al. |
| 2007/0092493 | A1 | 4/2007 | Sung et al. |
| 2007/0116678 | A1 | 5/2007 | Sung et al. |
| 2008/0021126 | A1 | 1/2008 | Dietliker et al. |
| 2008/0050423 | A1 | 2/2008 | Hsiue et al. |
| 2008/0118474 | A1 | 5/2008 | Okano et al. |
| 2010/0081750 | A1 | 4/2010 | Guire et al. |
| 2011/0020917 | A1 | 1/2011 | Wen et al. |

FOREIGN PATENT DOCUMENTS

| | | | |
|---|---|---|---|
| JP | 57117564 | | 7/1982 |
| JP | 59043061 | | 3/1984 |
| WO | 9316131 | | 8/1993 |
| WO | 9316176 | A1 | 8/1993 |
| WO | 9707161 | A1 | 2/1997 |
| WO | 9803489 | | 1/1998 |
| WO | 0126702 | A2 | 4/2001 |
| WO | 0140367 | | 6/2001 |
| WO | 03025267 | | 3/2003 |
| WO | 03097117 | A1 | 11/2003 |
| WO | 2004044281 | A2 | 5/2004 |
| WO | 2006135910 | A1 | 12/2006 |
| WO | 2007012050 | A2 | 1/2007 |
| WO | 2007144356 | A1 | 12/2007 |

OTHER PUBLICATIONS

Akiyama, Y., et al., Ultrathin Poly(N-isopropylacrylamide) Grafted Layer on Polystyrene Surfaces for Cell Adhesion/Detachment Control, Langmuir(20), p. 5506-5511 (2004).
Aoyagi, T., et al., Novel bifunctional polymer with reactivity and temperature sensitivity, J. Biomater. Sci. Polymer Edn. (11(1)), p. 101-110 (2000).
Canavan, H. et al., Cell sheet detachment affects the extracellular matrix: A surface science study comparing . . . , J. Biomed. Mater. Res. A.(75), p. 1-13 (2005).
Canavan, H., et al., Surface Characterization of the Extracellular Matrix Remaining after Cell Detachment from a Thermoresponsive Polymer, Langmuir(21), p. 1949-1955 (2005).
Chen, H., et al., Ultrafine Hydrogel Fibers with Dual Temperature- and pH-Responsive Swelling Behaviors, J. of Pol. Sci. A: Pol. Chem. (42) p. 6331-6339 (2004).
Da Silva, R., et al., Smart thermoresponsive coatings and surfaces for tissue engineering: switching cell-material boundaries, Trends in Biotech. (25(12)), p. 577-583 (2007).
Della Volpe, C., Wilhelmy Plate Measurements on Poly(N-isopropylacrylamide)-Grafted Surfaces, Langmuir(14), p. 4650-4656 (1998).
Gil, E.S., et al., Stimuli-responsive polymers and their bioconjugates, Prog. Polym. Sci.(29), p. 1173-1222 (2004).
Jin, Y., et al., Photocrosslinked Electrospun Chitosan-Based Biocompatible Nanofibers, J. of Applied Pol. Sci.(109), p. 3337-3343 (2008).
Kikuchi, A., et al., Nanostructured designs of biomedical materials: applications of cell sheet engineering . . . , J. of Controlled Rel.(101), p. 69-84 (2005).
Kim, DJ, et al., Formation of Thermoresponsive Poly(N-isopropylacrylamide)/Dextran Particles by Atom Transfer Radical Polymerization, Macromol. Rapid Comm(24), p. 517-521 (2003).
Ko, Y-G., et al., Development of Rapid Cell Recovery System Using Temperature-Responsive Nanofiber Surfaces, Key Engineering Materials (342-343), p. 249-252 (2007).
Kushida, A., et al., A noninvasive transfer system for polarized renal tubule epithelial cell sheets using temp.-resp. culture dishes, Euro. Cells & Mat.(10), p. 23-30 (2005).
Kushida, A., et al., Two-dimensional manipulation of differentiated Madin-Darby canine kidney (MDCK) cell sheets . . . , J. Biomed. Mat. Res. (54), p. 37-46 (2001).
Kwon, O.H., et al., Rapid cell sheet detachment from Poly(N-isopropylacrylamide)-grafted porous cell culture membranes, J. Biomed. Mat. Res.(50), p. 82-89 (2000).
Kwon, O.H., et al., Accelerated cell sheet recovery by co-grafting of PEG with PIPAAm onto porous cell culture membranes, Biomaterials(24), p. 1223-1232 (2003).
Li, Y.J., et al., Hydrogels as artificial matrices for human embryonic stem cell self-renewal, J. Biomed. Mater. Res. A, (79(A)), p. 1-5 (2006).
Liu, H., et al., Ionic-Strength and pH-Responsive Poly[acrylamide-co-(maleic acid)] Hydrogel Nanofibers, Macromol. Chem. and Phys. (208), p. 874-880 (2007).
Lutz, J-F., et al., Point by Point Comp. of Two Thermosensitive Polymers Exhibiting a Similar LCST: Is the Age of Poly (NIPAM) Over? J. Am. Chem. Soc.(128), p. 13046-13047 (2006).
Okano, T., et al., Mechanism of cell detachment from temperature-modulated, hydrophilic-hydrophobic polymer surfaces, Biomats. (16), p. 297-303 (1995).
Okuzaki, H., et al., Thermo-Responsive Nanofiber Mats, Macromolecules(42), p. 5916-5918 (2009).
Rothenberg, M. et al., Human and Rat Hepatocytes Cultured on Ultra-WebTM and Ultra-Web Polyamine Synth. Matrices show Enhanced Physiologic Activity . . . , Application Note (4 pgs).
Rothenberg, M. et al., Rat Hepatocyte Culture Physiology Shows Enhanced Cytochrome P450 Activity on a Synthetic Extracellular Matrix, Cell Notes(20), p. 18-20 (2008).
Shimizu, T., et al., Fabrication of Pulsatile Cardiac Tissue Grafts Using a Novel 3-Dimensional Cell Sheet Manipulation Technique . . . , Circulation Res., p. 1-9 (2002).
Takei, Y. et al., Dynamic Contact Angle Meas. of Temperature-Responsive Surface Prop. for Poly(N-isopropylacrylamide) Grafted Surfaces, Macromol. (27), p. 6163-6166 (1994).
Von Recum, H., et. al., Novel thermally reversible hydrogel as detachable cell culture substrate, J. Biomed. Mater. Res.(40), p. 631-639 (1998).
Yamato, M., Cell sheet engineering: from temperature-responsive culture surfaces to clinics, European Cells and Materials (6, Supp. 1), p. 26-27 (2003).
Allen, N. et al., Photochemistry and Photopolymerization Activity of Novel 4-Alkylamino Benzophenone Initiators, Eur. Polym. J.(26), p. 1345-1353 (1990).
Chua, K-N., et al., Stable immobilization of rat hepatocyte spheroids on galactosylated nanofiber scaffold, Biomaterials (26), p. 2537-2547 (2005).
Fang, J., et al., Applications of electrospun nanofibers, Chinese Science Bulletin(53), p. 2265-2286 (2008).
Geismann, C., et al., Photoreactive Functionalization of Poly(ethylene terephthalate) Track-Etched Pore Surfaces with "Smart" Polymer Systems, Macromol. Chem. Phys. (206), p. 268-281 (2005).
Kroschwitz, ed., Plastics, Concise Encyclopedia of Polymer Science and Engineering, John Wiley & Sons, 1990, p. 462-464.
Ma, Z., et al., Potential of Nanofiber Matrix as Tissue-Engineering Scaffolds, Tissue Engineering(11), p. 101-109 (2005).
Ma, Z., et al., Surface engineering of electrospun polyethylene terephthalate (PET) nanofibers towards development of a new material for blood vessel engineering, Biomaterials(26), p. 2527-2536 (2005).
Min, B.M., et al., Electrospinning of silk fibroin nanofibers and its effect on the adhesion and spreading of normal human keratinocytes and fibroblasts in vitro, Biomaterials(25), p. 1289-1297 (2004).

(56) References Cited

OTHER PUBLICATIONS

Sanders, J. et al., Fibro-porous meshes made from polyurethane micro-fibers: effects of surface charge on tissue response, Biomaterials(26), p. 813-818 (2005).

Shengguag, C., et al., Synthesis of pH-responsive crosslinked poly-[styrene-co-(maleic sodium anhydride)] and cellulose composite hydrogel nanofibers by electrospinning, Polym. Int.(58), p. 545-551 (2009).

Hungarian Intellectual Property Office Search Report, provided to the Intellectual Property Office of Singapore for corresponding Singapore Patent Application No. 200908547-3, which application is a National Stage application of PCT/US2008/067708, mailed Mar. 9, 2011 (7 pages).

Alvarez-Lorenzo et al., Reversible adsorption by a pH- and temperature-sensitive acrylic hydrogel, Journal of Controlled Release, vol. 80, pp. 247-257 (2002).

Kavanagh et al., Poly(N-isopropylacrylamide) copolymer films as vehicles for the sustained delivery of proteins to vascular endothelial cells, J. of Biomedical Materials Research Part A; vol. 72A, No. 1, pp. 25-35, published Jan. 1, 2005.

Kikuchi, A., et al., Nanostructured designs of biomedical materials: applications of cell sheet engineering to functional regenerative tissues and organs, J. of Controlled Release(101), p. 69-84 (2005).

Kobayashi, J. et al., Fabrication of a thermoresponsive cell culture dish: a key technology for cell sheet tissue engineering, Sci. Technol. Adv. Mater.(11), 12 pp. (2010).

Matsuda, N., et al., Tissue Engineering Based on Cell Sheet Technology, Adv. Mater.(19), p. 3089-3099 (2007).

Nagase, K., et al., Temperature-responsive intelligent interfaces for biomolecular separation and cell sheet engineering, J. R. Soc. Interface (6), p. 5293-5309 (2009).

Okano, T., et al., A novel recovery system for cultured cells using plasma-treated polystyrene dishes grafted with poly (N-isopropylacrylamide), J. of Biomed. Mats. Res.(27), p. 1243-1251 (1993).

Yamada, N., et al., Thermo-responsive polymeric surfaces; control of attachment and detachment of cultured cells, Makromol. Chem., Rapid Commun.(11), p. 571-576 (1990).

Yamato, M., et al., Nanofabrication for micropatterned cell arrays by combining electron beam-irradiated polymer grafting and localized laser ablation, J. Biomed. Mater. Res.(67A), p. 1065-1071 (2003).

Yoshida, R., et al., Comb-type grafted hydrogels with rapid de-swelling response to temperature changes, Nature(374), p. 240-242 (1995).

SEM image of PCL nanofiber showing bead free non defect nanofibers

Bright field image (scale bar = 200μm) of PIPAAm nanofibers

Protein adsorption profile of PIPAAm coated polystyrene at different temperatures Protein adsorption profile of PIPAAm coated nanofibers at 37°C and 20°C respectively PIPAAm + TriLite coated TCPS
Cell lift off time = 20 minutes Cell Seed Inc.
Cell lift off time = 20 minutes PIPAAm + TriLite coated nanofibers
Cell lift off time = 20 minutes Bare TCPS
No detachment Lift off times of BAEC cells cultured on various surfaces PIPAAm + TriLite coated TCPS
Cell lift off time = 40 minutes Cell Seed Inc.
Cell lift off time = 120 minutes + Gentle manipulation PIPAAm + TriLite coated nanofibers
Cell lift off time = 40 minutes Bare TCPS
No detachment Lift off times of T47-D cells cultured on various surfaces Replated BAEC cell sheet stained with anti conexxin 43

Bright field image of the replated BAEC cell sheet

BAEC cell sheets lifted off from thermo-responsive nanofibers surface and replated on fresh uncoated nanofibers

METHODS FOR PREPARING THERMALLY RESPONSIVE CELL CULTURE SURFACES

This application is a divisional of application Ser. No. 12/666,168, filed Jun. 23, 2010, now abandoned, which is a 371 of PCT/US08/67708, filed Jun. 20, 2008, which claims benefit of Application No. 60/945,801, filed Jun. 22, 2007.

This invention was made with government support under Grant No. 2R44GM081971, awarded by the National Institutes of Health. The government has certain rights in the invention.

TECHNICAL FIELD

The present invention generally relates to stimuli responsive nanofibers and stimuli responsive nanofiber modified surfaces. More particularly, the present invention is directed to nanofibers including a thermally responsive polymer, a multi-functional cross-linking agent, and optionally a biologically active material or a functional polymer that is reactive with a biologically active material. The stimuli responsive nanofibers can be used to modify a surface of a substrate, such as a cell culture device.

BACKGROUND

Nanofibers are being considered for a variety of applications because of their unique properties including high surface area, small fiber diameter, layer thinness, high permeability, and low basis weight. More attention has been focused on functionalized nanofibers having the capability of incorporating active chemistry, especially in biomedical applications such as wound dressing, biosensors and scaffolds for tissue engineering.

Nanofibers may be fabricated by electrostatic spinning (also referred to as electrospinning). The technique of electrospinning of liquids and/or solutions capable of forming fibers, is well known and has been described in a number of patents, such as, for example, U.S. Pat. Nos. 4,043,331 and 5,522,879. The process of electrospinning generally involves the introduction of a solution or liquid into an electric field, so that the solution or liquid is caused to produce fibers. These fibers are generally drawn to a conductor at an attractive electrical potential for collection. During the conversion of the solution or liquid into fibers, the fibers harden and/or dry. This hardening and/or drying may be caused by cooling of the liquid, i.e., where the liquid is normally a solid at room temperature; by evaporation of a solvent, e.g., by dehydration (physically induced hardening); or by a curing mechanism (chemically induced hardening).

The process of electrostatic spinning has typically been directed toward the use of the fibers to create a mat or other non-woven material, as disclosed, for example, in U.S. Pat. No. 4,043,331. Nanofibers ranging from 50 nm to 5 μm in diameter can be electrospun into a nonwoven or an aligned nanofiber mesh. Due to the small fiber diameters, electrospun textiles inherently possess a very high surface area and a small pore size. These properties make electrospun fabrics potential candidates for a number of applications including: membranes, tissue scaffolding, and other biomedical applications.

Nanofibers can be used to modify the surface of a substrate to achieve a desired surface characteristic. Most nanofiber surfaces have to be engineered to obtain the ability to immobilize biomolecules. Surface modification of synthetic biomaterials, with the intent to improve biocompatibility, has been extensively studied, and many common techniques have been considered for polymer nanofiber modification. For example, Sanders et al in "Fibro-Porous Meshes Made from Polyurethane Micro-Fibers: Effects of Surface Charge on Tissue Response" *Biomaterials* 26, 813-818 (2005) introduced different surface charges on electrospun polyurethane (PU) fiber surfaces through plasma-induced surface polymerization of negatively or positively charged monomers. The surface charged PU fiber mesh was implanted in rat subcutaneous dorsum for 5 weeks to evaluate tissue compatibility, and it was found that negatively charged surfaces may facilitate vessel ingrowth into the fibroporous mesh biomaterials. Ma et al. in "Surface Engineering of Electrospun Polyethylene Terephthalate (PET) Nanofibers Towards Development of a New Material for Blood Vessel Engineering" *Biomaterials* 26, 2527-2536 (2005) conjugated gelatin onto formaldehyde pretreated polyethylene terephthalate (PET) nanofibers through a grafted polymethacrylic acid spacer and found that the gelatin modification improved the spreading and proliferation of endothelial cells (ECs) on the PET nanofibers, and also preserved the EC's phenotype. Chua et al. in "Stable Immobilization of Rat Hepatocyte Spheroids on Galactosylated Nanofiber Scaffold" *Biomaterials* 26, 2537-2547 (2005) introduced galactose ligand onto poly(ε-caprolactone-co-ethyl ethylene phosphate) (PCLEEP) nanofiber scaffold via covalent conjugation to a poly(acrylic acid) spacer UV-grafted onto the fiber surface. Hepatocyte attachment, ammonia metabolism, albumin secretion and cytochrome P450 enzymatic activity were investigated on the 3-D galactosylated PCLEEP nanofiber scaffold as well as the functional 2-D film substrate.

SUMMARY

The methods and techniques summarized above are costly, complicated, or material specific. Thus, there is a need for a surface modification approach that is more general and easy to use and can be applied under mild conditions to a wide variety of nanofibers.

According to one embodiment, the present invention is a stimuli responsive nanofiber including a stimuli responsive polymer. One example of a stimuli responsive nanofiber is a thermally responsive nanofiber including a thermally responsive polymer. In either of these embodiments, the stimuli responsive nanofiber may include a cross-linking agent having at least two latent reactive activatable groups. In use, photochemically, electrochemically or thermally latent reactive groups will form covalent bonds when subjected to a source of energy. Suitable energy sources include radiation, electrical and thermal energy. In some embodiments, the radiation energy is visible, ultraviolet, infrared, x-ray or microwave electromagnetic radiation.

The cross-linking agent may have at least two latent reactive activatable groups. These latent reactive groups may be the same or may be different. For example, all of the latent reactive groups may be photochemically reactive groups. Alternatively, in other embodiments of the invention the cross-linking agent may include both photochemically and thermally reactive groups. Further, the cross-linking agent may be monomeric or polymeric materials or may be a mixture of both monomeric and polymeric materials.

According to a further embodiment of the present invention, the thermally responsive polymer is poly(isopropylacrylamide) as well as derivatives of poly(isopropylacrylamide) such as graft copolymer derivatives with polyethylene glycol derivatives.

According to another embodiment, the present invention is a method of treating a surface of a substrate including the steps of combining a stimuli responsive polymer, such as a thermally responsive polymer, and a cross-linking agent having at least two latent reactive activatable groups; forming at least one nanofiber from the combined mixture; contacting the surface with the nanofiber; and forming a bond between the nanofiber and the surface.

According to another embodiment, the present invention is a surface coating for a surface of an article. The surface coating includes a stimuli responsive nanofiber including a nanofiber coated with a stimuli responsive polymer, such as a thermally responsive polymer, and a cross-linking agent having at least two latent reactive activatable groups. Optionally, the coated nanofiber or the coated surface may include a biologically active material or, alternatively, a functional polymer.

According to yet another embodiment, the present invention is an article including a surface coating having a thermally responsive nanofiber. According to a further embodiment, the thermally responsive nanofiber includes a thermally responsive polymer and a cross-linking agent having at least two latent reactive activatable groups.

According to still yet another embodiment, the present invention is a cell culture device including a surface coating having a thermally responsive nanofiber. The thermally responsive nanofiber includes a thermally responsive polymer, a cross-linking agent having at least two latent reactive activatable groups, and a biologically active material.

According to other embodiments of the present invention, the stimuli responsive nanofiber may have a diameter ranging from 1 to 100 microns and still other embodiments may have a diameter ranging from 1 nm to 1000 nm. The stimuli responsive nanofiber may have an aspect ratio in a range of about at least 10 to at least 100.

According to yet a further embodiment of the present invention, the thermally responsive nanofiber has first physical property at a first predetermined temperature range and a second physical property at a second predetermined temperature range. The thermally responsive nanofiber is capable of transitioning from a first physical property to a second physical property upon the application or removal of heat to or from the system Various modifications and additions can be made to the exemplary embodiments discussed without departing from the scope of the present invention. For example, while the embodiments described above refer to particular features, the scope of this invention also includes embodiments having different combinations of features and embodiments that do not include all of the described features. Accordingly, the scope of the present invention is intended to embrace all such alternatives, modifications, and variations as fall within the scope of the claims, together with all equivalents thereof.

DESCRIPTION OF THE DRAWINGS

FIG. 7 is an electronic image of T47-D cells cultured on nanofiber and flat surfaces.

DETAILED DESCRIPTION

Figure 1:
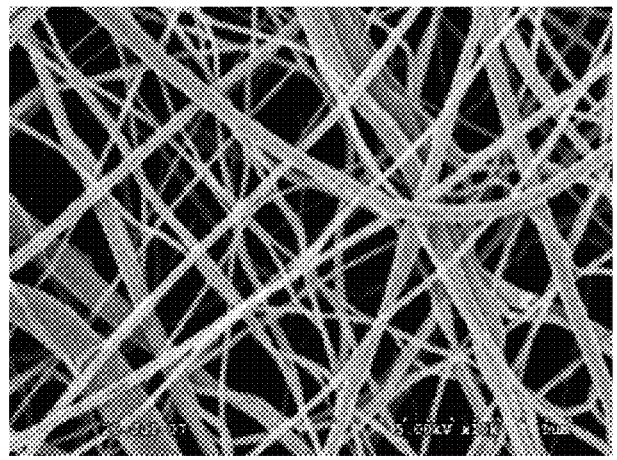
FIG. 1 is an electronic image of a polycaprolactone nanofiber described in Example 1.
Figure 2:
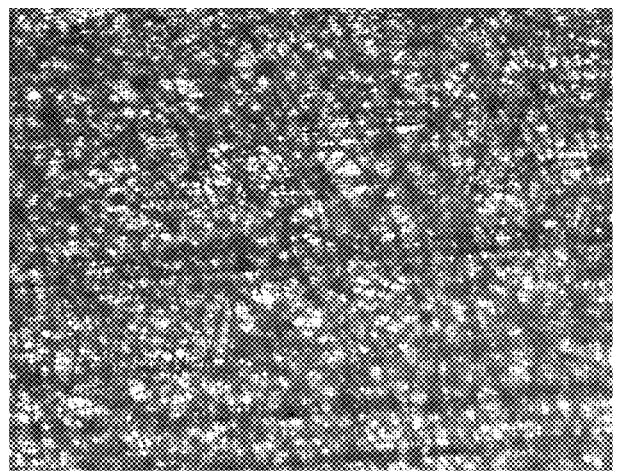
FIG. 2 is an electronic image of a polyisopropylacrylamide nanofiber described in Example 3.
Figure 3:
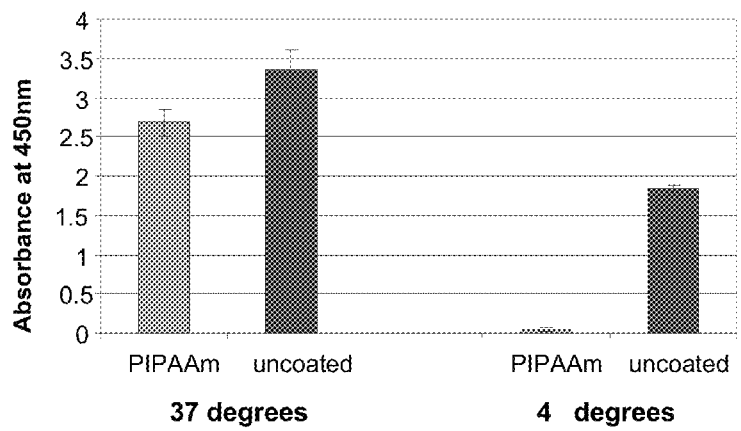
FIGS. 3 and 4 illustrate protein absorption profiles of polyisopropylacrylamide coated polystyrene and polyisopropylacrylamide nanofibers described in Example 4.
Figure 4:
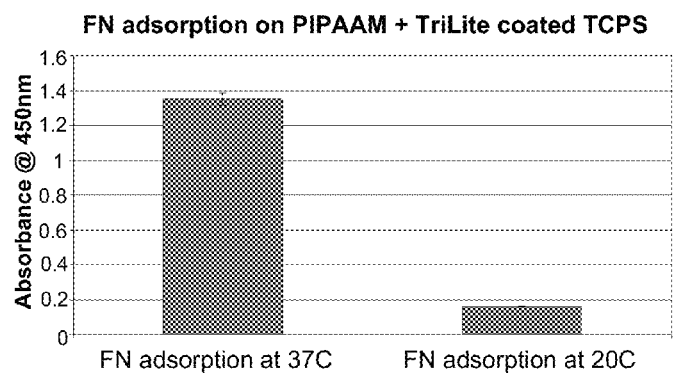

Stimuli responsive or "smart" materials are materials that have one or more properties that can be altered in a controlled fashion by the application of external stimuli, such as stress, temperature, moisture, pH, applied electric or magnetic fields, ionic strength, or biomolecules such as glucose or antigens. Representative stimuli responsive materials and polymers as well as their physical characteristic are reported by Gil et al., "Stimuli-responsive polymers and their bioconjugates," *Prog. Polym. Sci.*, 29, 1173-1222 (2004) which is incorporated by reference herein. A thermally responsive polymer is one example of these materials. A thermally responsive material is a material in which a physical property is altered in response to a change in temperature in the surrounding environment or system. A thermally responsive polymer may change from a hydrophilic state to hydrophobic state when the temperature of the system or its surroundings rises above a lower critical solution temperature (LCST). When in a hydrophilic state, the polymer chains become swollen. Conversely, in a hydrophobic state, the polymer chains collapse, and the polymer becomes insoluble in water. In most cases, the process can be reversible.

One embodiment of the present invention is directed to a thermally responsive nanofiber. The thermally responsive nanofiber can be used to modify a surface of a substrate to provide a functionalized surface. More particularly, the thermally responsive nanofiber can be used to provide a thermally responsive surface on a substrate. The physical property of the thermally responsive nanofiber modified surface of the substrate changes in response to a change in temperature in the system. Biologically active materials can be immobilized on the nanofiber modified surface by reacting with the functional groups accessible or exposed on the surface of the substrate. Typically, the biologically active materials retain all or a portion of their bioactivity after having been immobilized on the thermally responsive nanofiber modified surface. The ability of biologically active materials to bond with the surface of the substrate can be affected depending on the physical state of the modified surface. Thus, by controlling the temperature of the modified surface, the ability to bind to a biological material can be controlled.

According to one embodiment of the present invention the thermally responsive nanofiber includes a thermally responsive polymer, a biologically active material, and a cross-linking agent having at least two latent reactive activatable groups. The thermally responsive nanofiber can be used to modify the surface of a substrate by bonding the nanofiber to the surface by the formation of a covalent bond between the surface of the substrate and the nanofiber. At least one of the latent reactive activatable groups undergoes activation when subjected to a suitable energy source to form a covalent bond between the surface of the substrate and the thermally responsive nanofiber. The remaining latent reactive group(s) are left accessible or exposed on the surface of the substrate. The biologically active material included in the nanofiber or the accessible or exposed latent reactive groups on the surface may be used for further surface modification of the substrate.

A number of processing techniques such as drawing, template synthesis, phase separation, self-assembly or electrospinning have been used to prepare nanofibers.

For example, a thermally responsive nanofiber can be formed by electrospinning a fiber-forming combination that includes a thermally responsive polymer, a biologically active material, and a cross-linking agent having at least two latent reactive activatable groups. Electrospinning generally involves the introduction of a polymer or other fiber-forming solution or liquid into an electric field, so that the solution or liquid is caused to produce fibers. When a strong electrostatic field is applied to a fiber-forming combination held in a syringe with a capillary outlet, a pendant droplet of the fiber-forming mixture from the capillary outlet is deformed into a Taylor cone. When the voltage surpasses a threshold value, the electric forces overcome the surface tension on the droplet, and a charged jet of the solution or liquid is ejected from the tip of the Taylor cone. The ejected jet then moves toward a collecting metal screen that acts as a counterelectrode having a lower electrical potential. The jet is split into small charged fibers or fibrils and any solvent present evaporates leaving behind a nonwoven fabric mat formed on the screen.

In one embodiment, electrostatically spun fibers can be produced having very thin diameters. Parameters that influence the diameter, consistency, and uniformity of the electrospun fibers include the thermally responsive polymer, the molecular weight of the polymer; the cross-linker concentration (loading) in the fiber-forming mixture, the flow rate of the polymer solution, the applied voltage, and the needle collector distance. According to one embodiment of the present invention, a stimuli responsive nanofiber has a diameter ranging from about 1 nm to about 100 µm. In other embodiments, the stimuli responsive nanofiber has a diameter in a range of about 1 nm to about 1000 nm. Further, the nanofiber may have an aspect ratio in a range of about at least 10 to about at least 100. It will be appreciated that, because of the very small diameter of the fibers, the fibers have a high surface area per unit of mass. This high surface area to mass ratio permits fiber-forming material solutions to be transformed from solvated fiber-forming materials to solid nanofibers in fractions of a second.

The stimuli responsive polymer used to form the nanofiber may be selected from any stimuli responsive, fiber-forming material that is compatible with the cross-linking agent. In one embodiment, a selected thermally responsive polymer should be capable of undergoing a rapid change from a first physical property to a second physical property when the temperature of the system has risen above a lower critical solution temperature. Exemplary thermally responsive, fiber forming polymers include, but are not limited to, poly(isopropylacrylamide) and mixtures and copolymers thereof. Other thermally responsive polymers include random copolymers of 2-(2-methoxyethoxy)ethyl methacrylate and oligo(ethylene glycol) methacrylate.

According to one embodiment of the present invention, the thermally responsive polymer is poly(isopropylacrylamide). Poly(isopropylacrylamide) changes from a primarily hydrophobic state to a primarily hydrophilic state upon reaching a lower critical solution temperature of approximately 20 to 32° C. Poly-N-isopropylacrylamide (PIPAAm) has been one of the most studied thermo-responsive polymer not only because it displays a low critical solution temperature (LCST) of around 32° C., close to body temperature, but also because its LCST is relatively insensitive to environmental conditions. Slight variations of pH, concentration or chemical environment affect the LCST by only a few degrees. The main mechanism of PIPAAm's aqueous phase separation is the thermally induced release of water molecules bound to polymer isopropyl side groups, resulting in intra- and intermolecular hydrophobic interactions between isopropyl groups above the LCST.

The inclusion of cross-linking agents within the composition forming the thermally responsive nanofiber, allows the thermally responsive nanofiber to be compatible with a wide range of support surfaces. The latent reactive cross-linking agents can be used alone or in combination with other materials to provide a desired surface characteristic.

Suitable cross-linking agents include either monomeric (small molecule materials) or polymeric materials having at least two latent reactive activatable groups that are capable of forming covalent bonds with other materials when subjected to a source of energy such as radiation, electrical or thermal energy. In general, latent reactive activatable groups are chemical entities that respond to specific applied external energy or stimuli to generate active species with resultant covalent bonding to an adjacent chemical structure. Latent reactive groups are those groups that retain their covalent bonds under storage conditions but that form covalent bonds with other molecules upon activation by an external energy source. In some embodiments, latent reactive groups form active species such as free radicals. These free radicals may include nitrenes, carbine or excited states of ketones upon absorption of externally applied electric, electromagnetic or thermal energy. Various examples of known latent reactive groups are reported U.S. Pat. No. 4,973, U.S. Pat. No. 5,258,041 and U.S. Pat. No. 5,563,056.

Eight commercially available multifunctional photo-crosslinkers based on trichloromethyl triazine are available either from Aldrich Chemicals, Produits Chimiques Auxiliaires et de Syntheses, (Longjumeau, France), Shin-Nakamara Chemical, Midori Chemicals Co., Ltd. or Panchim S. A. (France). The eight compounds include 2,4,6-tris(trichloromethyl)-1,3,5 triazine, 2-(methyl)-4,6-bis(trichloromethyl)-1,3,5-triazine, 2-(4-methoxynaphthyl)-4,6-bis(trichloromethyl)-1,3,5-triazine, 2-(4-ethoxynaphthyl)-4,6-bis(trichloromethyl)-1,3,5-triazine, 4-(4-carboxylphenyl)-2,6-bis(trichloromethyl)-1,3,5-triazine, 2-(4-methoxyphenyl)-4,6-bis(trichloromethyl)-1,3,5-triazine, 2-(1-ethen-2-2'-furyl)-4,6-bis(trichloromethyl)-1,3,5-triazine and 2-(4-methoxystyryl)-4,6-bis(trichloromethyl)-1,3,5-triazine.

In some embodiments, the latent reactive groups are the same, while in other embodiments the latent reactive groups may be different. For example, the latent reactive groups may be two different groups that are both activated by radiation. In other embodiments one latent reactive group may by activated by radiation while another latent reactive group may be activated by heat. Suitable cross-linking agents include bi-, tri- and multi-functional monomeric and polymeric materials.

Latent reactive groups that are reactive to thermal or heat energy include a variety of reactive moieties and may include known compounds that decompose thermally to form reactive species that will then form covalent bonds. The covalent bonds allow the cross-linking to bind to adjacent materials. Suitable thermally-reactive groups typically have a pair of atoms having a heat sensitive or labile bond. Heat labile bonds include oxygen-oxygen bonds such as peroxide bonds, nitrogen-oxygen bonds, and nitrogen-nitrogen bonds. Such bonds will react or decompose at temperatures in a range of not more than 80-200° C.

Both thermally generated carbenes and nitrenes undergo a variety of chemical reactions, including carbon bond insertion, migration, hydrogen abstraction, and dimerization. Examples of carbene generators include diazirines and diazo-compounds. Examples of nitrene generators include aryl azides, particularly perfluorinated aryl azides, acyl azides, and triazolium ylides. In addition, groups that upon heating form reactive triplet states, such as dioxetanes, or radical anions and radical cations may also be used to form the thermally-reactive group.

In one embodiment the thermally-reactive group of the cross-linking agent includes a peroxide —(O—O)— group. Thermally-reactive peroxide-containing groups include, for example, thermally-reactive diacyl peroxide groups, thermally-reactive peroxydicarbonate groups, thermally-reactive dialkylperoxide groups, thermally-reactive peroxyester groups, thermally-reactive peroxyketal groups, and thermally-reactive dioxetane groups.

Dioxetanes are four-membered cyclic peroxides that react or decompose at lower temperatures compared to standard peroxides due to the ring strain of the molecules. The initial step in the decomposition of dioxetanes is cleavage of the O—O bond, the second step breaks the C—C bond creating one carbonyl in the excited triplet state, and one in an excited singlet state. The excited triplet state carbonyl can extract a hydrogen from an adjacent material, forming two radical species, one on the adjacent material and one on the carbon of the carbonyl with the oxygen and will form a new covalent bond between the thermally reactive dioxetane and the adjacent material.

Representative thermally reactive moieties are reported in US 20060030669 and other representative thermal latent reactive groups are reported in U.S. Pat. No. 5,258,041. Both of these documents are hereby incorporated by reference.

Latent reactive groups that are reactive to electromagnetic radiation, such as ultraviolet or visible radiation, are typically referred to as photochemical reactive groups.

The use of latent reactive activatable species in the form of latent reactive activatable aryl ketones is useful. Exemplary latent reactive activatable aryl ketones include acetophenone, benzophenone, anthraquinone, anthrone, anthrone-like heterocycles (i.e., heterocyclic analogs of anthrone such as those having N, O, or S in the 10-position), and their substituted (e.g., ring substituted) derivatives. Examples of aryl ketones include heterocyclic derivatives of anthrone, including acridone, xanthone, and thioxanthone, and their ring substituted derivatives. In particular, thioxanthone, and its derivatives, having excitation energies greater than about 360 nm are useful.

The functional groups of such ketones are suitable since they are readily capable of undergoing an activation/inactivation/reactivation cycle. Benzophenone is an exemplary photochemically reactive activatable group, since it is capable of photochemical excitation with the initial formation of an excited singlet state that undergoes intersystem crossing to the triplet state. The excited triplet state can insert into carbon-hydrogen bonds by abstraction of a hydrogen atom (from a support surface, for example), thus creating a radical pair. Subsequent collapse of the radical pair leads to formation of a new carbon-carbon bond. If a reactive bond (e.g., carbon-hydrogen) is not available for bonding, the ultraviolet light-induced excitation of the benzophenone group is reversible and the molecule returns to ground state energy level upon removal of the energy source. Photochemically reactive activatable aryl ketones such as benzophenone and acetophenone are of particular importance inasmuch as these groups are subject to multiple reactivation in water and hence provide increased coating efficiency.

In some embodiments of the invention, photochemically reactive cross-linking agents may be derived from three different types of molecular families. Some families include one or more hydrophilic portions, i.e., a hydroxyl group (that may be protected), amines, alkoxy groups, etc. Other families may include hydrophobic and amphiphilic portions. In one embodiment, the family has the formula:

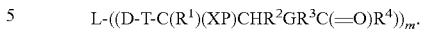

L is a linking group. D is O, S, SO, $SO_2$, $NR^5$ or $CR^6R^7$. T is $(-CH_2-)_x$, $(-CH_2CH_2-O-)_x$, $(-CH_2CH_2CH_2-O-)_x$ or $(-CH_2CH_2CH_2CH_2-O-)_x$. $R^1$ is a hydrogen atom, an alkyl, alkyloxyalkyl, aryl, aryloxyalkyl or aryloxyaryl group. X is O, S, or $NR^8R^9$. P is a hydrogen atom or a protecting group, with the proviso that P is absent when X is $NR^8R^9$. $R^2$ is a hydrogen atom, an alkyl, alkyloxyalkyl, aryl, aryloxyalkyl or aryloxyaryl group. G is O, S, SO, $SO_2$, $NR^{10}$, $(CH_2)_r$—O— or C=O. $R^3$ and $R^4$ are each independently an alkyl, aryl, arylalkyl, heteroaryl, or a heteroarylalkyl group or when $R^3$ and $R^4$ are tethered together via $(-CH_2-)_q$, $(-CH_2-)_rC=O(-CH_2-)_s$, $(-CH_2-)_rS(-CH_2-)_s$, $(-CH_2-)_rS=O(-CH_2-)_s$, $(-CH_2-)_rS(O)_2(-CH_2-)_s$, or $(-CH_2-)_rNR(-CH_2-)_s$. $R^5$ and $R^{10}$ are each independently a hydrogen atom or an alkyl, aryl, or arylalkyl group. $R^6$ and $R^7$ are each independently a hydrogen atom, an alkyl, aryl, arylalkyl, heteroaryl or heteroarylalkyl group. $R^8$ and $R^9$ are each independently a hydrogen atom, an alkyl, aryl, or arylalkyl group, R is a hydrogen atom, an alkyl group or an aryl group, q is an integer from 1 to about 7, r is an integer from 0 to about 3, s is an integer from 0 to about 3, m is an integer from 2 to about 10, t is an integer from 1 to about 10 and x is an integer from 1 to about 500.

In one embodiment, L is a branched or unbranched alkyl chain having between about 2 and about 10 carbon atoms.

In another embodiment, D is an oxygen atom (O).

In still another embodiment, T is $(-CH_2-)_x$ or $(-CH_2CH_2-O-)_x$ and x is 1 or 2.

In still yet another embodiment, $R^1$ is a hydrogen atom.

In yet another embodiment, X is an oxygen atom, O, and P is a hydrogen atom.

In another embodiment, $R^2$ is a hydrogen atom.

In still another embodiment, G is an oxygen atom, O.

In still yet another embodiment, $R^3$ and $R^4$ are each individually aryl groups, which can be further substituted, and m is 3.

In one particular embodiment, L is

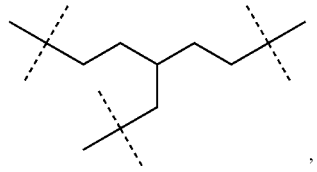

D is O, T is $(-CH_2-)_x$, $R^1$ is a hydrogen atom, X is O, P is a hydrogen atom, $R^2$ is a hydrogen atom, G is O, $R^3$ and $R^4$ are phenyl groups, m is 3 and x is 1.

In yet another particular embodiment, L is $(-CH_2-)_y$, D is O, T is $(-CH_2-)_x$, $R^1$ is a hydrogen atom, X is O, P is a hydrogen atom, $R^2$ is a hydrogen atom, G is O, $R^3$ and $R^4$ are phenyl groups, m is 2, x is 1 and y is an integer from 2 to about 6, and in particular, y is 2, 4 or 6.

In certain embodiments, x is an integer from about 1 to about 500, more particularly from about 1 to about 400, from about 1 to about 250, from about 1 to about 200, from about 1 to about 150, from about 1 to about 100, from about 1 to about 50, from about 1 to about 25 or from about 1 to about 10.

In another embodiment, the family has the formula:

and L, T, $R^1$, X, P, $R^2$, G, $R^3$, $R^4$, $R^8$, $R^9$, $R^{10}$, R, q, r, s, m, t and x are as defined above.

In one embodiment, L has a formula according to structure (I):

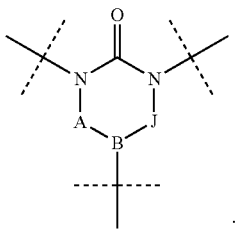

(I)

A and J are each independently a hydrogen atom, an alkyl group, an aryl group, or together with B form a cyclic ring, provided when A and J are each independently a hydrogen atom, an alkyl group, or an aryl group then B is not present, B is $NR^{11}$, O, or $(-CH_2-)_z$, provided when A, B and J form a ring, then A and J are $(-CH_2-)_z$ or C=O, $R^{11}$ is a hydrogen atom, an alkyl group, an aryl group or denotes a bond with T, each z independently is an integer from 0 to 3 and provided when either A or J is C=O, then B is $NR^{11}$, O, or $(-CH_2-)_z$ and z must be at least 1.

In another embodiment, T is $-CH_2-$.

In another embodiment, the family has the formula: L-((GTZR$^3$C(=O)R$^4$))$_m$, and L, T, G, $R^3$, $R^4$, $R^{10}$, R, q, r, s, m, t and x are as defined above. Z can be a C=O, COO or CONH when T is $(-CH_2-)_x$.

In one embodiment, L has a formula according to structure (I):

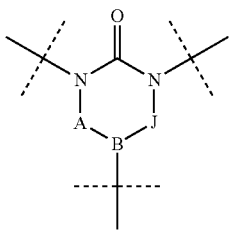

(I)

and A, B, J, $R^{11}$, and z are as defined above.

In another embodiment, L has a formula according to structure (II):

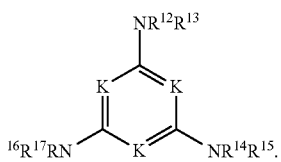

(II)

$R^{12}$, $R^{13}$, $R^{14}$, $R^{15}$, $R^{16}$, $R^{17}$ are each independently a hydrogen atom, an alkyl or aryl group or denotes a bond with T, provided at least two of $R^{12}$, $R^{13}$, $R^{14}$, $R^{15}$, $R^{16}$, $R^{17}$ are bonded with T and each K, independently is CH or N.

In another embodiment, the family has the formula:

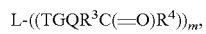

L, G, $R^3$, $R^4$, $R^{10}$, R, q, r, s, m, t and x are as defined above. T is $(-CH_2-)_x$, $(-CH_2CH_2-O-)_x$, $(-CH_2CH_2CH_2-O-)_x$, $(-CH_2CH_2CH_2CH_2-O-)_x$ or forms a bond. Q is $(-CH_2-)_p$, $(-CH_2CH_2O-)_p$, $(-CH_2CH_2CH_2-O-)_p$ or $(-CH_2CH_2CH_2CH_2-O-)_p$ and p is an integer from 1 to about 10.

In one embodiment, L has a formula according to structure (I):

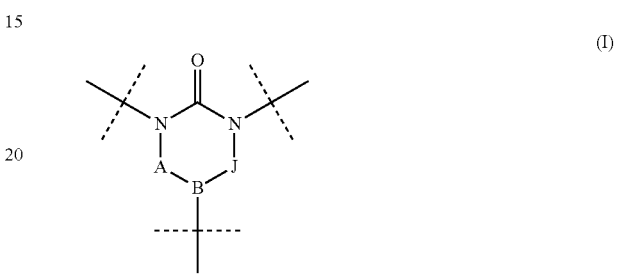

(I)

A, B, J, $R^{11}$, and z are as defined above.

In another embodiment, L has a formula according to structure (II):

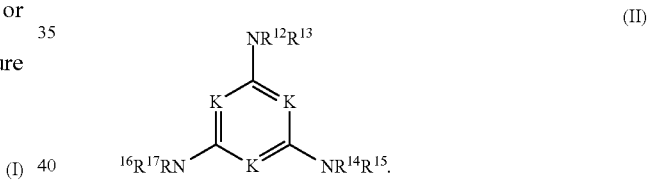

(II)

$R^{12}$, $R^{13}$, $R^{14}$, $R^{15}$, $R^{16}$, $R^{17}$ are each independently a hydrogen atom, an alkyl or aryl group or denotes a bond with T, provided at least two of $R^{12}$, $R^{13}$, $R^{14}$, $R^{15}$, $R^{16}$, $R^{17}$ are bonded with T and each K, independently is CH or N.

In still yet another embodiment, compounds of the present invention provide that $R^3$ and $R^4$ are both phenyl groups and are tethered together via a CO, a S or a $CH_2$.

In yet another embodiment, compounds of the present invention provide when $R^3$ and $R^4$ are phenyl groups, the phenyl groups can each independently be substituted with at least one alkyloxyalkyl group, such as $CH_3O-(CH_2CH_2O-)_n-$, or $CH_3O(-CH_2CH_2CH_2O-)_n-$ a hydroxylated alkoxy group, such as $HO-CH_2CH_2O-$, $HO(-CH_2CH_2O-)_n-$ or $HO(-CH_2CH_2CH_2O-)_n-$, etc. wherein n is an integer from 1 to about 10.

In another embodiment the family has the formula:

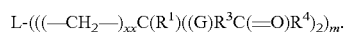

L, each R, $R^1$, each G, each $R^3$, each $R^4$, each $R^{10}$, each q, each r, each s, each t and m are as defined above and xx is an integer from 1 to about 10.

In one embodiment, L has a formula according to structure (I):

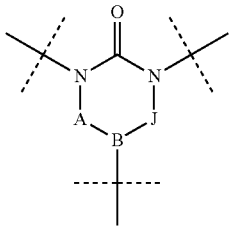

A, B, J, $R^{11}$, and z are as defined above.

In another embodiment, A and B are both hydrogen atoms.

In still another embodiment, xx is 1.

In yet another embodiment, $R^1$ is H.

In still yet another embodiment, G is (—$CH_2$—)$_t$O— and t is 1.

In another embodiment, $R^3$ and $R^4$ are each individually aryl groups.

In still yet another embodiment, xx is 1, $R^1$ is H, each G is (—$CH_2$—)$_t$O—, t is 1 and each of $R^3$ and $R^4$ are each individually aryl groups.

In another embodiment of the invention, the family has the formula:

L, R, $R^1$, $R^2$, $R^3$, $R^4$, $R^8$, $R^9$, $R^{10}$, X, P, G, q, r, s, t, and m are as defined above.

In one embodiment, L is

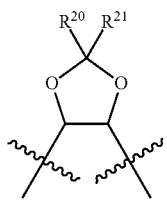

and $R^{20}$ and $R^{21}$ are each individually a hydrogen atom, an alkyl group or an aryl group.

In another embodiment, $R^1$ is H.

In still another embodiment, wherein X is O.

In yet another embodiment, P is H.

In still yet another embodiment, $R^2$ is H.

In another embodiment, G is (—$CH_2$—)$_t$O— and t is 1.

In still another embodiment, $R^3$ and $R^4$ are each individually aryl groups.

In yet another embodiment, $R^1$ is H, X is O, P is H, $R^2$ is H, G is (—$CH_2$—)$_t$O—, t is 1, $R^3$ and $R^4$ are each individually aryl groups and $R^{20}$ and $R^{21}$ are both methyl groups.

In yet another embodiment, the present invention provides a family of compounds having the formula:

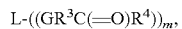

L is a linking group; G is O, S, SO, $SO_2$, $NR^{10}$, ($CH_2$)$_t$—O— or C=O; $R^3$ and $R^4$ are each independently an alkyl, aryl, arylalkyl, heteroaryl, or an heteroarylalkyl group or when $R^3$ and $R^4$ are tethered together via (—$CH_2$—)$_q$, (—$CH_2$—)$_r$C=O(—$CH_2$—)$_s$, (—$CH_2$—)$_r$S(—$CH_2$—)$_s$, (—$CH_2$—)$_r$S=O(—$CH_2$—)$_s$ or (—$CH_2$—)$_r$S(O)$_2$(—$CH_2$—)$_s$, (—$CH_2$—)$_r$NR(—$CH_2$—)$_s$; $R^{10}$ is a hydrogen atom or an alkyl, aryl, or an arylalkyl group; R is a hydrogen atom, an alkyl or an aryl group; q is an integer from 1 to about 7; r is an integer from 0 to about 3; s is an integer from 0 to about 3; m is an integer from 2 to about 10; and t is an integer from 1 to about 10.

In one embodiment, L is

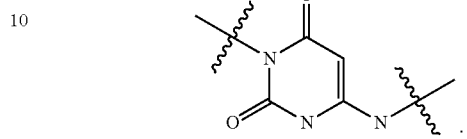

In another embodiment, G is C=O.

In still another embodiment, $R^3$ and $R^4$ are each individually aryl groups.

In yet another embodiment, G is C=O and $R^3$ and $R^4$ are each individually aryl groups.

"Alkyl" by itself or as part of another substituent refers to a saturated or unsaturated branched, straight-chain or cyclic monovalent hydrocarbon radical having the stated number of carbon atoms (i.e., $C_1$-$C_6$ means one to six carbon atoms) that is derived by the removal of one hydrogen atom from a single carbon atom of a parent alkane, alkene or alkyne. Typical alkyl groups include, but are not limited to, methyl; ethyls such as ethanyl, ethenyl, ethynyl; propyls such as propan-1-yl, propan-2-yl, cyclopropan-1-yl, prop-1-en-1-yl, prop-1-en-2-yl, prop-2-en-1-yl, cycloprop-1-en-1-yl; cycloprop-2-en-1-yl, prop-1-yn-1-yl, prop-2-yn-1-yl, etc.; butyls such as butan-1-yl, butan-2-yl, 2-methyl-propan-1-yl, 2-methyl-propan-2-yl, cyclobutan-1-yl, but-1-en-1-yl, but-1-en-2-yl, 2-methyl-prop-1-en-1-yl, but-2-en-1-yl, but-2-en-2-yl, buta-1,3-dien-1-yl, buta-1,3-dien-2-yl, cyclobut-1-en-1-yl, cyclobut-1-en-3-yl, cyclobuta-1,3-dien-1-yl, but-1-yn-1-yl, but-1-yn-3-yl, but-3-yn-1-yl, etc.; and the like. Where specific levels of saturation are intended, the nomenclature "alkanyl," "alkenyl" and/or "alkynyl" is used, as defined below. "Lower alkyl" refers to alkyl groups having from 1 to 6 carbon atoms.

"Alkanyl" by itself or as part of another substituent refers to a saturated branched, straight-chain or cyclic alkyl derived by the removal of one hydrogen atom from a single carbon atom of a parent alkane. Typical alkanyl groups include, but are not limited to, methanyl; ethanyl; propanyls such as propan-1-yl, propan-2-yl (isopropyl), cyclopropan-1-yl, etc.; butanyls such as butan-1-yl, butan-2-yl (sec-butyl), 2-methyl-propan-1-yl (isobutyl), 2-methyl-propan-2-yl (t-butyl), cyclobutan-1-yl, etc.; and the like.

"Alkenyl" by itself or as part of another substituent refers to an unsaturated branched, straight-chain or cyclic alkyl having at least one carbon-carbon double bond derived by the removal of one hydrogen atom from a single carbon atom of a parent alkene. The group may be in either the cis or trans conformation about the double bond(s). Typical alkenyl groups include, but are not limited to, ethenyl; propenyls such as prop-1-en-1-yl, prop-1-en-2-yl, prop-2-en-1-yl, prop-2-en-2-yl, cycloprop-1-en-1-yl; cycloprop-2-en-1-yl; butenyls such as but-1-en-1-yl, but-1-en-2-yl, 2-methyl-prop-1-en-1-yl, but-2-en-1-yl, but-2-en-2-yl, buta-1,3-dien-1-yl, buta-1,3-dien-2-yl, cyclobut-1-en-1-yl, cyclobut-1-en-3-yl, cyclobuta-1,3-dien-1-yl, etc.; and the like.

"Alkyloxyalkyl" refers to a moiety having two alkyl groups tethered together via an oxygen bond. Suitable alkyloxyalkyl groups include polyoxyalkylenes, such as polyethyleneoxides, polypropyleneoxides, etc. that are terminated with an alkyl group, such as a methyl group. A general formula for such compounds can be depicted as R'—(OR")$_n$ or (R'O)$_n$—R" wherein n is an integer from 1 to about 10, and R' and R" are alkyl or alkylene groups.

"Alkynyl" by itself or as part of another substituent refers to an unsaturated branched, straight-chain or cyclic alkyl having at least one carbon-carbon triple bond derived by the removal of one hydrogen atom from a single carbon atom of a parent alkyne. Typical alkynyl groups include, but are not limited to, ethynyl; propynyls such as prop-1-yn-1-yl, prop-2-yn-1-yl, etc.; butynyls such as but-1-yn-1-yl, but-1-yn-3-yl, but-3-yn-1-yl, etc.; and the like.

"Alkyldiyl" by itself or as part of another substituent refers to a saturated or unsaturated, branched, straight-chain or cyclic divalent hydrocarbon group having the stated number of carbon atoms (i.e., $C_1$-$C_6$ means from one to six carbon atoms) derived by the removal of one hydrogen atom from each of two different carbon atoms of a parent alkane, alkene or alkyne, or by the removal of two hydrogen atoms from a single carbon atom of a parent alkane, alkene or alkyne. The two monovalent radical centers or each valency of the divalent radical center can form bonds with the same or different atoms. Typical alkyldiyl groups include, but are not limited to, methandiyl; ethyldiyls such as ethan-1,1-diyl, ethan-1,2-diyl, ethen-1,1-diyl, ethen-1,2-diyl; propyldiyls such as propan-1,1-diyl, propan-1,2-diyl, propan-2,2-diyl, propan-1,3-diyl, cyclopropan-1,1-diyl, cyclopropan-1,2-diyl, prop-1-en-1,1-diyl, prop-1-en-1,2-diyl, prop-2-en-1,2-diyl, prop-1-en-1,3-diyl, cycloprop-1-en-1,2-diyl, cycloprop-2-en-1,2-diyl, cycloprop-2-en-1,1-diyl, prop-1-yn-1,3-diyl, etc.; butyldiyls such as, butan-1,1-diyl, butan-1,2-diyl, butan-1,3-diyl, butan-1,4-diyl, butan-2,2-diyl, 2-methyl-propan-1,1-diyl, 2-methyl-propan-1,2-diyl, cyclobutan-1,1-diyl; cyclobutan-1,2-diyl, cyclobutan-1,3-diyl, but-1-en-1,1-diyl, but-1-en-1,2-diyl, but-1-en-1,3-diyl, but-1-en-1,4-diyl, 2-methyl-prop-1-en-1,1-diyl, 2-methanylidene-propan-1,1-diyl, buta-1,3-dien-1,1-diyl, buta-1,3-dien-1,2-diyl, buta-1,3-dien-1,3-diyl, buta-1,3-dien-1,4-diyl, cyclobut-1-en-1,2-diyl, cyclobut-1-en-1,3-diyl, cyclobut-2-en-1,2-diyl, cyclobuta-1,3-dien-1,2-diyl, cyclobuta-1,3-dien-1,3-diyl, but-1-yn-1,3-diyl, but-1-yn-1,4-diyl, buta-1,3-diyn-1,4-diyl, etc.; and the like. Where specific levels of saturation are intended, the nomenclature alkanyldiyl, alkenyldiyl and/or alkynyldiyl is used. Where it is specifically intended that the two valencies be on the same carbon atom, the nomenclature "alkylidene" is used. A "lower alkyldiyl" is an alkyldiyl group having from 1 to 6 carbon atoms. In some embodiments the alkyldiyl groups are saturated acyclic alkanyldiyl groups in which the radical centers are at the terminal carbons, e.g., methandiyl (methano); ethan-1,2-diyl (ethano); propan-1,3-diyl (propano); butan-1,4-diyl (butano); and the like (also referred to as alkylenes, defined infra).

"Alkylene" by itself or as part of another substituent refers to a straight-chain saturated or unsaturated alkyldiyl group having two terminal monovalent radical centers derived by the removal of one hydrogen atom from each of the two terminal carbon atoms of straight-chain parent alkane, alkene or alkyne. The location of a double bond or triple bond, if present, in a particular alkylene is indicated in square brackets. Typical alkylene groups include, but are not limited to, methylene (methano); ethylenes such as ethano, etheno, ethyno; propylenes such as propano, prop[1]eno, propa[1,2]dieno, prop[1]yno, etc.; butylenes such as butano, but[1]eno, but[2]eno, buta[1,3]dieno, but[1]yno, but[2]yno, buta[1,3]diyno, etc.; and the like. Where specific levels of saturation are intended, the nomenclature alkano, alkeno and/or alkyno is used. In some embodiments, the alkylene group is ($C_1$-$C_6$) or ($C_1$-$C_3$) alkylene. Other embodiments include straight-chain saturated alkano groups, e.g., methano, ethano, propano, butano, and the like.

"Aryl" by itself or as part of another substituent refers to a monovalent aromatic hydrocarbon group having the stated number of carbon atoms (i.e., $C_5$-$C_{15}$ means from 5 to 15 carbon atoms) derived by the removal of one hydrogen atom from a single carbon atom of a parent aromatic ring system. Typical aryl groups include, but are not limited to, groups derived from aceanthrylene, acenaphthylene, acephenanthrylene, anthracene, azulene, benzene, chrysene, coronene, fluoranthene, fluorene, hexacene, hexaphene, hexylene, as-indacene, s-indacene, indane, indene, naphthalene, octacene, octaphene, octalene, ovalene, penta-2,4-diene, pentacene, pentalene, pentaphene, perylene, phenalene, phenanthrene, picene, pleiadene, pyrene, pyranthrene, rubicene, triphenylene, trinaphthalene, and the like, as well as the various hydro isomers thereof. In some embodiments, the aryl group is ($C_5$-$C_{15}$) aryl or, alternatively, ($C_5$-$C_{10}$) aryl. Other embodiments include phenyl and naphthyl.

"Arylalkyl" by itself or as part of another substituent refers to an acyclic alkyl radical in which one of the hydrogen atoms bonded to a carbon atom, typically a terminal or sp$^3$ carbon atom, is replaced with an aryl group. Typical arylalkyl groups include, but are not limited to, benzyl, 2-phenylethan-1-yl, 2-phenylethen-1-yl, naphthylmethyl, 2-naphthylethan-1-yl, 2-naphthylethen-1-yl, naphthobenzyl, 2-naphthophenylethan-1-yl and the like. Where specific alkyl moieties are intended, the nomenclature arylalkanyl, arylalkenyl and/or arylalkynyl is used. In some embodiments, the arylalkyl group is ($C_7$-$C_{30}$) arylalkyl, e.g., the alkanyl, alkenyl or alkynyl moiety of the arylalkyl group is ($C_1$-$C_{10}$) and the aryl moiety is ($C_6$-$C_{20}$) or, alternatively, an arylalkyl group is ($C_7$-$C_{20}$) arylalkyl, e.g., the alkanyl, alkenyl or alkynyl moiety of the arylalkyl group is ($C_1$-$C_8$) and the aryl moiety is ($C_6$-$C_{12}$).

"Aryloxyalkyl" refers to a moiety having an aryl group and an alkyl group tethered together via an oxygen bond. Suitable aryloxyalkyl groups include phenyloxyalkylenes, such as methoxyphenyl or ethoxyphenyl.

"Cycloalkyl" by itself or as part of another substituent refers to a cyclic version of an "alkyl" group. Typical cycloalkyl groups include, but are not limited to, cyclopropyl; cyclobutyls such as cyclobutanyl and cyclobutenyl; cyclopentyls such as cyclopentanyl and cycloalkenyl; cyclohexyls such as cyclohexanyl and cyclohexenyl; and the like.

"Cycloheteroalkyl" by itself or as part of another substituent refers to a saturated or unsaturated cyclic alkyl radical in which one or more carbon atoms (and any associated hydrogen atoms) are independently replaced with the same or different heteroatom. Typical heteroatoms to replace the carbon atom(s) include, but are not limited to, N, P, O, S or Si. Where a specific level of saturation is intended, the nomenclature "cycloheteroalkanyl" or "cycloheteroalkenyl" is used. Typical cycloheteroalkyl groups include, but are not limited to, groups derived from epoxides, imidazolidine, morpholine, piperazine, piperidine, pyrazolidine, pyrrolidine, quinuclidine, and the like.

"Halogen" or "Halo" by themselves or as part of another substituent, unless otherwise stated, refer to fluoro, chloro, bromo and iodo.

"Haloalkyl" by itself or as part of another substituent refers to an alkyl group in which one or more of the hydrogen atoms are replaced with a halogen. Thus, the term "haloalkyl" is meant to include monohaloalkyls, dihaloalkyls, trihaloalkyls, etc. up to perhaloalkyls. For example, the expression "($C_1$-

$C_2$) haloalkyl" includes fluoromethyl, difluoromethyl, trifluoromethyl, 1-fluoroethyl, 1,1-difluoroethyl, 1,2-difluoroethyl, 1,1,1-trifluoroethyl or perfluoroethyl.

"Heteroalkyl, Heteroalkanyl, Heteroalkenyl, Heteroalkynyl" by itself or as part of another substituent refer to alkyl, alkanyl, alkenyl and alkynyl radical, respectively, in which one or more of the carbon atoms (and any associated hydrogen atoms) are each independently replaced with the same or different heteroatomic groups. Typical heteroatomic groups include, but are not limited to, —O—, —S—, —O—O—, —S—S—, —O—S—, —NR'—, =N—N=, —N=N—, —N=N—NR'—, —PH—, —P(O)$_2$—, —O—P(O)$_2$—, —S(O)—, —S(O)$_2$—, -SnH$_2$— and the like, where R' is hydrogen, alkyl, substituted alkyl, cycloalkyl, substituted cycloalkyl, aryl or substituted aryl.

"Heteroaryl" by itself or as part of another substituent, refers to a monovalent heteroaromatic radical derived by the removal of one hydrogen atom from a single atom of a parent heteroaromatic ring system. Typical heteroaryl groups include, but are not limited to, groups derived from acridine, arsindole, carbazole, β-carboline, benzoxazine, benzimidazole, chromane, chromene, cinnoline, furan, imidazole, indazole, indole, indoline, indolizine, isobenzofuran, isochromene, isoindole, isoindoline, isoquinoline, isothiazole, isoxazole, naphthyridine, oxadiazole, oxazole, perimidine, phenanthridine, phenanthroline, phenazine, phthalazine, pteridine, purine, pyran, pyrazine, pyrazole, pyridazine, pyridine, pyrimidine, pyrrole, pyrrolizine, quinazoline, quinoline, quinolizine, quinoxaline, tetrazole, thiadiazole, thiazole, thiophene, triazole, xanthene, and the like. The heteroaryl group may be from 5-20 membered heteroaryl or, alternatively, from 5-10 membered heteroaryl. In some embodiments, the heteroaryl groups are those derived from thiophene, pyrrole, benzothiophene, benzofuran, indole, pyridine, quinoline, imidazole, oxazole and pyrazine.

"Heteroarylalkyl" by itself or as part of another substituent refers to an acyclic alkyl group in which one of the hydrogen atoms bonded to a carbon atom, typically a terminal or sp$^3$ carbon atom, is replaced with a heteroaryl group. Where specific alkyl moieties are intended, the nomenclature heteroarylalkanyl, heteroarylakenyl and/or heteroarylalkynyl is used. In some embodiments, the heteroarylalkyl group is a 6-21 membered heteroarylalkyl, e.g., the alkanyl, alkenyl or alkynyl moiety of the heteroarylalkyl is ($C_1$-$C_6$) alkyl and the heteroaryl moiety is a 5-15-membered heteroaryl. In other embodiments, the heteroarylalkyl is a 6-13 membered heteroarylalkyl, e.g., the alkanyl, alkenyl or alkynyl moiety is ($C_1$-$C_3$) alkyl and the heteroaryl moiety is a 5-10 membered heteroaryl.

"Hydroxyalkyl" by itself or as part of another substituent refers to an alkyl group in which one or more of the hydrogen atoms are replaced with a hydroxyl substituent. Thus, the term "hydroxyalkyl" is meant to include monohydroxyalkyls, dihydroxyalkyls or trihydroxyalkyls.

"Parent Aromatic Ring System" refers to an unsaturated cyclic or polycyclic ring system having a conjugated π electron system. Specifically included within the definition of "parent aromatic ring system" are fused ring systems in which one or more of the rings are aromatic and one or more of the rings are saturated or unsaturated, such as, for example, fluorene, indane, indene, phenalene, tetrahydronaphthalene, etc. Typical parent aromatic ring systems include, but are not limited to, aceanthrylene, acenaphthylene, acephenanthrylene, anthracene, azulene, benzene, chrysene, coronene, fluoranthene, fluorene, hexacene, hexaphene, hexylene, s-indacene, indane, indene, naphthalene, octacene, octaphene, octalene, ovalene, penta-2,4-diene, pentacene, pentalene, pentaphene, perylene, phenalene, phenanthrene, picene, pleiadene, pyrene, pyranthrene, rubicene, tetrahydronaphthalene, triphenylene, trinaphthalene, and the like, as well as the various hydro isomers thereof.

"Parent Heteroaromatic Ring System" refers to a parent aromatic ring system in which one or more carbon atoms (and any associated hydrogen atoms) are independently replaced with the same or different heteroatom. Typical heteroatoms to replace the carbon atoms include, but are not limited to, N, P, O, S, Si, etc. Specifically included within the definition of "parent heteroaromatic ring systems" are fused ring systems in which one or more of the rings are aromatic and one or more of the rings are saturated or unsaturated, such as, for example, arsindole, benzodioxan, benzofuran, chromane, chromene, indole, indoline, xanthene, etc. Typical parent heteroaromatic ring systems include, but are not limited to, arsindole, carbazole, β-carboline, chromane, chromene, cinnoline, furan, imidazole, indazole, indole, indoline, indolizine, isobenzofuran, isochromene, isoindole, isoindoline, isoquinoline, isothiazole, isoxazole, naphthyridine, oxadiazole, oxazole, perimidine, phenanthridine, phenanthroline, phenazine, phthalazine, pteridine, purine, pyran, pyrazine, pyrazole, pyridazine, pyridine, pyrimidine, pyrrole, pyrrolizine, quinazoline, quinoline, quinolizine, quinoxaline, tetrazole, thiadiazole, thiazole, thiophene, triazole, xanthene, and the like.

"Leaving group" is a group that is displaced during a reaction by a nucleophilic reagent. Suitable leaving groups include S(O)$_2$Me, —SMe or halo (e.g., F, Cl, Br, I).

"Linking group" is a group that serves as an intermediate locus between two or more end groups. The nature of the linking group can vary widely, and can include virtually any combination of atoms or groups useful for spacing one molecular moiety from another. For example, the linker may be an acyclic hydrocarbon bridge (e.g., a saturated or unsaturated alkyleno such as methano, ethano, etheno, propano, prop[1]eno, butano, but[1]eno, but[2]eno, buta[1,3]dieno, and the like), a monocyclic or polycyclic hydrocarbon bridge (e.g., [1,2]benzeno, [2,3]naphthaleno, and the like), a simple acyclic heteroatomic or heteroalkyldiyl bridge (e.g., —O—, —S—, —S—O—, —NH—, —PH—, —C(O)—, —C(O)NH—, —S(O)—, —S(O)$_2$—, —S(O)NH—, —S(O)$_2$NH—, —O—CH$_2$—, —CH$_2$—O—CH$_2$—, —O—CH=CH—CH$_2$—, and the like), a monocyclic or polycyclic heteroaryl bridge (e.g., [3,4]furano, pyridino, thiopheno, piperidino, piperazino, pyrazidino, pyrrolidino, and the like) or combinations of such bridges.

"Protecting group" is a group that is appended to, for example, a hydroxyloxygen in place of a labile hydrogen atom. Suitable hydroxyl protecting group(s) include esters (acetate, ethylacetate), ethers (methyl, ethyl), ethoxylated derivatives (ethylene glycol, propylene glycol) and the like that can be removed under either acidic or basic conditions so that the protecting group is removed and replaced with a hydrogen atom. Guidance for selecting appropriate protecting groups, as well as synthetic strategies for their attachment and removal, may be found, for example, in Greene & Wuts, *Protective Groups in Organic Synthesis,* 3d Edition, John Wiley & Sons, Inc., New York (1999) and the references cited therein (hereinafter "Greene & Wuts").

Plastics or porous membranes such as polyolefins, polystyrenes, poly(methyl)methacrylates, polyacrylonitriles, poly(vinylacetates), poly (vinyl alcohols), chlorine-containing polymers such as poly(vinyl) chloride, polyoxymethylenes, polycarbonates, polyamides, polyimides, polyurethanes, phenolics, amino-epoxy resins, polyesters, silicones, cellulose-based plastics, fluoropolymers and rubber-like plastics can all be used as supports, providing surfaces that can be modified as described herein. In addition, supports such as those formed of pyrolytic carbon, parylene coated surfaces, and silylated surfaces of glass, ceramic, or metal are suitable for surface modification.

The method of the present invention may involve the attachment of a biologically active material to a support surface. For example, a thermally responsive nanofiber including a cross-linking agent is provided having two or more latent reactive activatable groups in the presence of a support surface. According to an alternative embodiment, the nanofiber may also include a biologically active material or a functional polymer that is reactive with a biologically active material. At least one of the latent reactive groups is activated and covalently bonded to the surface. The remaining latent reactive groups are allowed to remain in their inactive state and are later activated in order to bind a biologically active material or a functional polymer in order to attach the biologically active material to the surface of the substrate.

A functional polymer is a polymer having one or more functional groups that will react with a biologically active material. Representative functional groups include carboxy, ester, epoxy, hydroxyl, amido, amino, thio N-hydroxy succinimide, isocyanate, anhydride, azide, aldehyde, cyanuryl chloride or phosphine groups that will react with a biologically active material Alternatively, the biologically active material or functional polymer provided in the thermally responsive nanofiber composition may bind to a second biological material in order to attach the second biological material to the surface of the substrate through manipulation of the physical properties of the support surface via, for example, the application or removal of heat from the system.

The steps of the method can be performed in any suitable order. For example, a thermally responsive nanofiber including a thermally responsive polymer and cross-linking agent, as described herein, may be physically absorbed in or adsorbed to a suitable support surface by hydrophobic interactions. Upon photoactivation, at least one of the photoactivatable groups (e.g., benzophenone groups) undergoes covalent bond formation at the support surface. With the absence of abstractable hydrogens in the proximity of the remaining unbonded photoactivatable group(s), and removal of the photoactivation source, the photoactivatable group returns from an excited state to a ground state. These remaining photoactivatable groups are then capable of being reactivated when a biologically active material intended for immobilization is present, and when the treated surface is exposed to another round of illumination. This method can be described as a "two-step" approach, where the thermally responsive nanofiber is applied in the first step to create a latent reactive surface, and in the second step, the biologically active material is added for attachment to the activated surface.

Alternatively, the method, described as a "one-step" method, provides that the thermally responsive nanofibers of the present invention are mixed together with the biologically active material to form a composition. The resultant composition is used to surface modify materials in a single photoactivation step. In this case, photoactivation triggers not only covalent bond formation of at least one photoactivatable group with the surface of the substrate, but also simultaneously triggers covalent bond formation with any adjacent biologically active materials residing on the surface.

In an alternative embodiment, the thermally responsive nanofiber is formed from a combination or mixture including a thermally responsive polymer, a cross-linking agent having at least two latent activatable groups, and a biologically active material. At least one of the latent reactive groups undergoes covalent bond formation at the support surface to bond the nanofiber to the surface of the substrate. The remaining latent reactive group(s) can undergo photoactivation to react with a second biologically active material. Alternatively, the biologically active material incorporated into the nanofiber can itself react with a second biologically active material to provide for further functionalization of the substrate.

In another alternative method, the thermally responsive nanofibers of the present invention are used to pretreat a substrate surface prior to the application and bonding of molecules that have themselves been functionalized with latent reactive groups. This method is useful in situations where a particularly difficult substrate requires maximal coating durability. In this manner, the number of covalent bonds formed between the substrate surface and the target molecule derivatized with latent reactive groups can typically be increased, as compared to surface modification with a desired latent reactive group-containing target molecule alone.

After the surface of a substrate has been coated or treated with the thermally responsive nanofibers of the present invention, the thermally responsive surface can then be fine tuned by the application or removal of heat to the system to selectively bind and release a biological material of interest. Heat can be applied to the system to transition the thermally responsive nanofiber bound to the surface from a hydrophilic state to a hydrophobic state. In a hydrophobic state at a temperature higher than LCST, the polymer chains collapse and the surface becomes hydrophobic. In this state the thermally responsive nanofiber surface may attract or repel select target molecules. Alternatively, heat can also be removed from the system by cooling the substrate below the LCST. Once cooled, the thermally responsive nanofiber may revert back to its initial hydrophilic state, once again showing an altered affinity for a particular target molecule.

Suitable biologically active or target molecules for use in the present invention encompass a diverse group of materials or substances. These materials may be used in either an underivatized form or previously derivatized. Moreover, target molecules can be immobilized singly or in combination with other types of target molecules.

Target molecules can be immobilized to the surface after (e.g., sequentially) the surface has been primed with the thermally responsive nanofibers of the present invention. Alternatively, target molecules are immobilized during (e.g., simultaneously with) attachment of the thermally responsive nanofibers to the surface of the substrate.

Typically, target molecules are selected so as to confer particular desired properties to the surface and/or to the device or article bearing the surface. According to one embodiment of the present invention, the target molecule or material is a biologically active material. Biologically active materials which may be immobilized on the surface of the nanofiber modified substrate, or alternatively, provided as a part of the nanofiber composition, generally include, but are not limited to, the following: enzymes, proteins, carbohydrates, nucleic acids, and mixtures thereof. Further examples of suitable target molecules, including biological materials, and the surface properties they are typically used to provide, is represented by the following nonlimiting list.

| TARGET MOLECULE | FUNCTIONAL ACTIVITY |
|---|---|
| Synthetic Polymers | |
| Sulfonic acid-substituted polyacrylamide | Lubricity, negatively charged surface, hydrophilicity |
| Polyacrylamide | Lubricity, protein repulsion, hydrophilicity |

-continued

| TARGET MOLECULE | FUNCTIONAL ACTIVITY |
| --- | --- |
| Polyethylene glycol | Lubricity, cell and protein repulsion, hydrophilicity |
| Polyethyleneimine | Positively charged surface |
| Polylactic acid | Bioerodible surface |
| Polyvinyl alcohol | Lubricity, hydrophilicity |
| Polyvinyl pyrrolidone | Lubricity, hydrophilicity |
| Quaternary amine-substituted polyacrylamide | Lubricity, positively charged surface |
| Silicone | Lubricity, hydrophobicity |
| Conductive polymeric materials, e.g., polyvinylpyridine, polyacetylene, polypyrrole) | Electric conductivity |
| Carbohydrates | |
| Alginic acid | Lubricity, hydrophilicity |
| Cellulose | Lubricity, hydrophilicity, bio-degradable glucose source |
| Chitosan | Positively charged surface, hydrophilicity, hemostatsis |
| Glycogen | Hydrophilicity, biodegradable glucose source |
| Heparin | Antithrombogenicity, hydrophilicity, cell and growth factor attachment, protein affinity |
| Hyaluronic acid | Lubricity, negatively charged surface |
| Pectin | Lubricity, hydrophilicity |
| Mono-, di-saccharides | Hydrophilicity |
| Dextran sulfate | Chromatography media, hydrophilicity |
| Proteins | |
| Antibodies | Antigen binding, immunoassay |
| Antithrombotic agents (e.g. antithrombin III) | Antithrombogenic surface |
| Albumin | Nonthrombogenic surface |
| Attachment proteins/peptides (e.g. collagen) | Cell attachment |
| Enzymes | Catalytic surface |
| Extracellular matrix proteins/peptides | Cell attachment and growth |
| Growth factors, proteins/peptides | Cell growth |
| Hirudin | Antithrombogenic surface |
| Thrombolytic proteins (e.g., streptokinase, plasmin, urokinase) | Thrombolytic activity |
| Lipids | |
| Fatty acids | Hydrophobicity, biocompatibility |
| Mono-, di-and triglycerides | Hydrophobicity, lubricity, bio-degradable fatty acid source |
| Phospholipids | Hydrophobicity, lubricity, bio-degradable fatty acid source |
| Prostaglandins/leukotrienes | Nonthrombogenic surface/immobilized messenger |
| Nucleic Acids | |
| DNA | Substrate for nucleases/affinity binding, genomic assay |
| RNA | Substrate for nucleases/affinity binding, genomic assay |
| Nucleosides, nucleotides | Source of purines, pyrimidines, enzyme cofactor |
| Drugs/vitamins/cofactors | |
| Enzyme cofactors | Immobilized enzyme |
| Heme compounds | Globin bindings/surface oxygenation |
| Drugs | Drug activity |
| Nonpolymeric Materials | |
| Dyes (e.g., azo dyestuffs) | Coloring agent |
| Fluorescent compounds (e.g., fluorescein) | Fuorescence |

The thermally responsive nanofibers of the present invention can be used in a wide variety of applications including: filters, scaffolds for tissue engineering, protective clothing, reinforcement of composite materials, and sensor technologies.

Medical articles that can be fabricated from or coated or treated with the thermally responsive nanofibers of the present invention can include, but are not limited to, the following: catheters including urinary catheters and vascular catheters (e.g., peripheral and central vascular catheters), wound drainage tubes, arterial grafts, soft tissue patches, gloves, shunts, stents, tracheal catheters, wound dressings, sutures, guide wires and prosthetic devices (e.g., heart valves and LVADs). Vascular catheters which can be prepared according to the present invention include, but are not limited to, single and multiple lumen central venous catheters, peripherally inserted central venous catheters, emergency infusion catheters, percutaneous sheath introducer systems, thermodilution catheters, including the hubs and ports of such vascular catheters, leads to electronic devices such as pacemakers, defibrillators, artificial hearts, and implanted biosensors.

Additional articles that can be fabricated from or have a surface that can be coated or treated with the thermally responsive nanofibers of the present invention can include, but are not limited to, the following: slides, multi-well plates, Petri dishes, tissue culture slides, tissue culture plates, tissue culture flasks, cell culture devices, or column supports and/or chromatography media.

In another embodiment, the thermally responsive nanofibers of the present invention can be applied to a microscope slide or "chip" for biomolecule immobilization.

In yet another embodiment, the thermally responsive nanofibers of the present invention can be applied to a surface of a cell culture device to provide a thermally responsive surface Various types of mammalian cells have been seeded on tissue culture polystyrene (TCPS) coated with poly-isopropylacrylamide (PIPAAm). The cells adhered, proliferated and differentiated in the same manner as uncoated TCPS. With the cells on bare TCPS, digestive trypsin treatment is carried out to dissolve the extracellular matrix and to chelate and remove Ca ions to release the cells, which in the process lose their cell surface receptors, gap junctions and underlying extracellular matrix. Another alternative for cell release is the use of cell scrapers, the mechanical use of which generates irregularly shaped tissue fragments. With thermo-responsive polymer coated dishes the cells are detached in a non invasive fashion only by reducing the culture temperature from 20°-32° C. at a temperature at which the polymer hydrates. In contrast to enzymatic digestion, both adhesive proteins and cell-cell junctions between the confluent cells are preserved, enabling generation of a three dimensional functional tissue that lacks any scaffold.

Cell sheet engineering is a unique technique that has arisen from the use of thermo-responsive polymer as a cell culture substrate. At 37° C., PIPAAm becomes hydrophobic, promoting protein adsorption and thereby cell adhesion. By lowering the temperature to 20°-32° C., cells can be released from the underlying substrate. The change from hydrophobic to hydrophilic character over this transition results in the release of proteins and adherent cells from the culture substrate. Through this technique, cell-cell contacts, gap junctions and surface receptors are maintained as well as the underlying extracellular matrix (ECM). The intact ECM serves as glue to layer cell sheets to form homogenous tissue grafts for example highly pulsatile cardiac tissue grafts or heterogeneous tissue grafts by layering sheets from various different cell types, for example endothelial cells and hepatocytes. The cell sheets thus generated have been highly applicable to animal transplant studies. Transplant experiments have been done to compare the response of dissociated cells versus cell sheet injections. Dissociated cardiomyocytes equivalent to four cell sheets were injected into left subcutaneous dorsal tissue and four cell sheet layers obtained from low temperature lift off mediated by thermo-responsive polymer, were transplanted into the right subcutaneous tissue. The isolated cells formed a lump under the skin while the sheet transplanted site remained smooth. One week after the transplant, the respective sites were opened and cross sectional views of the right side indicated a flat square cardiac graft with no visible necrosis and connexin 43 (a gap junction marker) staining revealed the presence of numerous gap junctions.

The left side showed cell dense graft surface zones with central cell-void areas and only a few depositions were seen when stained for connexin 43. The grafting of PIPAAm on tissue culture polystyrene and its success with the culture and harvest of various cell types has led to the development of commercially available tissue culture polystyrene dishes by Cell Seed Inc. (Tokyo, Japan). The use of these surfaces completely abandons the use of trypsin when collecting cells as detachment is achieved by lowering the culture temperature. This eliminates the use of laborious pipetting, saving on both labor, time and cell/tissue damage.

The culture surfaces can also be functionalized by co-polymerization of PIPAAm with its carboxylate derivatized analog, 2-carboxylsopropylacrylamide (CIPAAm). Insulin was immobilized on culture surfaces by standard amide bond formation with the CIPAAm carboxylate group. The surfaces with immobilized insulin showed an increase in proliferation of bovine carotid artery endothelial (BAEC) cells even without the addition of serum. Similarly, the carboxyl groups on CIPPAm sequences can be used to immobilize cell adhesive sequences such as RGDS which promotes BAEC cell adhesion and proliferation without the addition of fetal bovine serum in the culture medium. Thus, the culture of cells and their low temperature lift off obviates the need of using serum which has both cost and safety (prions and bovine spongiform encephalopathy) concerns regarding its use. These surfaces would be useful for serum free culture of cells and cell sheets which can then be used in various tissue engineering and transplant applications.

The spontaneous cell sheet generation from PIPAAm—grafted TCPS is a relatively slow process, occurring gradually from the sheet periphery toward the interior. Thus, significant incubation time is required to lift up the intact, viable cell sheet completely. Rapid recovery of cell sheets is considered important to maintain biological function and viability of recovered cell sheets, as well as for practical assembly of tissue structures. The rate limiting step to cell recovery is the hydration of hydrophobized PIPAAm segments interacting with the cell sheet, incorporation of a highly water permeable substrate to interface is desirable between cell sheets and the thermo-responsive surfaces. Several approaches have been tried in this regard to make the detachment of cell sheets a faster process. It has been shown that placing hydrophilically-modified PVDF membranes on confluent Madin-Darby canine kidney (MDCK) cells incubated at 20° C. for one hour helps in the easy lift of cells. Another set of experiments has utilized porous membranes (PET) grafted with PIPAAm. As mentioned earlier, on PIPAAm-grafted TCPS dishes, water required to hydrate PIPAAm at a lower temperature can readily penetrate the culture matrix from only the periphery of each cell to the interface between the cell and grafted PIPAAm chains. On porous membranes, water hydration of PIPAAm is supplied through pores underneath adherent cells, as well as from the periphery of each cell. Ready, rapid access of bulk water to PIPAAm grafts through pores beneath attached cells should accelerate single cell and cell sheet detachment. The pore size of a membrane is an important factor in determining the cell adhesion and growth. In general, cells do not grow on surfaces which have a pore size greater than their pseudopodium. On membranes with pore size greater than 5um the fibroblast adhesion and suppression was found to be greatly reduced.

Nanofibers produced via the process of electrospinning may have unprecedented porosity (>70%), a high surface to volume ratio, and a wide range of pore diameter distribution and high interconnectivity, all physical properties ideal for promoting cell attachment and growth. Furthermore, the nanotopography of electrospun nanofibers closely resembles the nanofibrillar and nanoporous 3D geometry of the ECM and basement membrane. The higher surface area allows for a higher percentage of cellular attachment as well as for multiple focal adhesion points on different fibers due to nano-sized fiber diameters. Because the diameters of nanofibers are orders of magnitude smaller than the size of the cells, cells are able to organize, spread or attach to adsorbed proteins at multiple focal points.

Electrospun nanofibers are capable of supporting a wide variety of cell types. Human umbilical cord endothelial cells attached and proliferated better when seeded onto 50:50 poly (L-lactic acid-co-ε-caprolactone) (PLCL) fibers with a diameter of 300 nm compared to 7 μm microfibers. Cells attached to microfibers were round in shape and non-proliferative, whereas on nanofibers, the cells were nicely spread out and anchored on multiple fibers. Elias and co-workers have reported osteoblast adhesion, proliferation, alkaline phosphatase activity and ECM secretion on carbon nanofibers increased with decreasing fiber diameter in the range of 60-200 nm. Nanogrooved surfaces can induce contact guidance of human corneal epithelial cells, causing them to elongate and align their cytoskeleton along the topological features. Highly porous PLLA scaffolds with nanoscale pores created using a liquid-liquid phase separation have been used for the culture of neural stem cells and were shown to have a positive effect on neurite outgrowth. Recent studies show that the growth of NIH 3T3 fibroblasts and normal rat kidney cells on polyamide nanofibrillar surfaces resulted in changes in morphology, actin organization, focal adhesion assembly, fibronectin secretion and rates of cell proliferation that are more representative of fibroblast phenotype in vivo. Breast epithelial cells on the same surface underwent morphogenesis to form multicellular spheroids unlike the same cells cultured on glass. It has also been shown that the commercially available polyamide nanofibers provide a better substrate for cell attachment for weakly adherent cell lines, for example PC12, a neuronal cell line. Polyamide electrospun nanofibers have also been shown to support the attachment and proliferation of mouse embryonic stem cells (ES-D3). These cells differentiated into neurons, oligodendrocytes and astrocytes based upon the culture media selected. Fetal bovine chondrocytes seeded on nanofibers poly (ε-caprolactone) (PCL) scaffolds were able to maintain the chondrocytic phenotype during three weeks of culture, specifically upregulating collagen type IIB expression, indicative of mature chondrocyte phenotype. These studies demonstrate that nanofiber scaffolds are not only cytocompatible but can also be used to stimulate and encourage cell proliferation and phenotypic behavior.

To induce specific biological responses from the attached cells, the nanofibers may also be functionalized using bioactive molecules. Functionalization is typically carried out by either conjugating the molecules to the surface of the nanofibers or by incorporating the bioactive molecules in the spinning solution. Polyacrylic acid (PAA) grafted onto poly (ε-caprolactone-coethyl ethylene phosphate) (PCLEEP) allows for the conjugation of galactose ligand, which mediates hepatocytes attachment. Hepatocytes cultured on these PCLEEP functionalized nanofiber scaffolds formed 20-100 μm spheroid aggregates that engulfed the nanofibers. To underscore the importance of culture substrate, others have shown that aminated nanofiber meshes supported a higher degree of cell adhesion and proliferation of hematopoietic stem/progenitor cells compared to aminated films. Similarly conjugation of bone morphogenetic protein-2 (BMP-2) on chitosan nanofibers resulted in better proliferation, alkaline phosphatase activity and calcium deposition of osteoblastic cells.

In sum, the nanoscale nature of the electrospun polymeric nanofibers mimics the natural ECM. ECM—like properties of the nanofibers can be used to stimulate and encourage cell proliferation and differentiation. Moreover, the cells are able to maintain their in vivo like morphology and function. Thus, the combination of fiber composition, morphology, alignment and the capacity to incorporate bioactive molecules or growth factors helps recreate the functions of native ECM.

The invention will be further described with reference to the following nonlimiting examples. It will be apparent to those skilled in the art that many changes can be made in the embodiments described without departing from the scope of the present invention. Thus the scope of the present invention should not be limited to the embodiments described in this application, but only by embodiments described by the language of the claims and the equivalents of those embodiments. Unless otherwise indicated, all percentages are by weight.

EXAMPLES

Example 1

Electrospinning of PCL and PS Nanofibers

Poly (ε-caprolactone) (PCL), with an average molecular weight of 80 kDa and Polystyrene (350,000 Da) were purchased from Aldrich chemicals (Milwaukee, Wis.). 0.14 g/ml solutions were prepared by dissolving 14 g of PCL or PS in 100 ml of organic solvent mixture (1:1) composed of tetrahydrofuran (Fisher Scientific) and N,N-dimethylformamide (Alfa Aesar, Ward Hill, Mass.) and mixing it well by shaking the mixture for 24 h at room temperature. The polymer solution was placed in a plastic syringe fitted with a 27 G blunt needle (Strategic Applications, Inc., Libertyville, Ill.). A syringe pump (KD Scientific, USA) was used to feed the polymer solution into the needle tip. Nanofiber meshes were fabricated by electrospinning using a high voltage power supply (Gamma High Voltage Research, USA). The nanofibers were collected onto grounded aluminum foil located at a fixed distance from the needle tip. The meshes were then removed, placed in a vacuum chamber for at least 48 h to remove organic solvent residue and then stored in a dessicator. The nanofibers were evaluated with a microscope (Olympus BX 60).

Parameters that significantly influence the diameter, consistency and uniformity of the electrospun PCL and PS fibers were polymer concentration, applied voltage, solution feeding rate and needle-collector distance. These parameters were optimized until unbeaded and uniform fibers were spun continuously without needle clogging. Three polymer concentrations (0.10 g/ml, 0.12 g/ml, and 0.14 g/ml), two voltages (17 kv, 20 kv) and three needle-collector distances (8 cm, 12 cm, 15 cm) were investigated to obtain non-defect nanofibers. The optimized conditions are shown in Table 1.

TABLE 1

| Electrospinning parameters | |
|---|---|
| Polymer concentration | 0.14 g/ml |
| Applied voltage | 20 kv |
| Flow rate | 0.02 ml/min |
| Needle-collector distance | 12 cm |

FIG. 1. shows the typical SEM image of PCL nanofibers. The average fiber diameter of nanofibers is, 453±146 nm. Highly porous structure was observed in the formulation tested. The porosity measured by a liquid displacement method was 0.90

Example 2

Coating of Nanofiber Meshes with (PIPAAm)

Various coating approaches were employed to obtain a thin coating of the thermo-responsive polymer on different culture substrates. The substrates included TCPS, Thermanox coverslips (Nunc), commercially available nanofiber meshes (Surmodics Inc., Corning Inc.) and in-house PCL nanofibers. The Thermanox coverslips and nanofiber inserts were dip coated in an IPA (isopropyl alcohol) solution of 20 mg/ml PIPAAm (polyisopropylacrylamide Aldrich chemicals, Mw+20-25 KDa, WI) and 0.8 mg/ml TriLite (tris[2-hydroxy-3-(4-benzoylphenoxy)propl]isocyanurate. The pieces were dip coated by immersing in the coating solution for 10 seconds and then extracted at a speed of 0.5 cm/sec. The meshes were air dried and then UV illuminated (300-400 nm, Harland Medical UVM400, MN) for 5 minutes. Various dipping speeds, concentrations, number of dips and immerse times were tried. The efficacy of the coated surfaces was tested by the attachment and detachment behavior of the BAEC cells (Lonza Biosciences, NJ, USA) at 37° C. and 20° C. respectively. Although the above mentioned conditions worked well for cell attachment and detachment, this dipping method could not coat the tissue culture formatted surfaces (for example, multi well dishes or 100 mm dishes). Therefore, another approach was tried where the multi well dishes, nanofiber inserts, commercially available nanofiber 96 well and 100 mm dishes were first coated with 0.8 mg/ml solution of TriLite. The TriLite solution was immediately withdrawn and UV illuminated for 30 seconds. PIPAAm solution (20 mg/ml in IPA) was then added to the wells, immediately withdrawn and UV illuminated for 2.0 minutes. The treated surfaces were rinsed with IPA and tissue culture grade sterile water before plating the cells.

Example 3

Smart Polymer Nanofibers

Four formulations containing 1.0 wt % TriLite were prepared to synthesize smart polymer photoreactive nanofibers. These formulations were PS in (DMF/THF), PCL in (DMF/THF), PIPAAm in (IPA/DMF), PIPAAm-co-PEG (1%) in water. The nanofibers were fabricated by the electrospinning process of Example 2. The parameters such as, polymer concentration, solvent ratio, applied voltage and needle-collector distance, were optimized until unbeaded and uniform fibers with an average diameter under 500 nm can be spun continuously without needle clogging. The optimized conditions are shown in Table 2. After drying, all the nanofibers except PS and PCL were illuminated for 5 minutes under a UV lamp (Harland Medical UVM400, Eden Prairie, Minn.). The nanofibers were evaluated under a microscope. PEG-PI-PAAm was synthesized by free radical copolymerization of N-isopropylacrylamide (Aldrich) with poly (ethyleneglycol) methyl ether methacrylate (Mw 2,000, Aldrich) in water using ammonium persulfate (Sigma) as initiator and N,N,N', N'-tetramethylethylenediamine (Aldrich) as a catalyst.

TABLE 2

| Polymer | Solvent | Polymer Concentration | Applied Voltage | Feeding Rate ml/min | Needle-Collector Distance |
|---|---|---|---|---|---|
| PS | THF/DMF | 14% | 20 kv | .02 | 12 cm |
| PCL | THF/DMF | 14% | 20 kv | .02 | 12 cm |
| PIPAAm | IPA/DMF | 25% | 16 kv | 0.1 | 6 cm |
| PEG-PIPAAm | water | 5% | 16 kv | 0.2 | 6 cm |

Example 4

Surface Characterization and Screening of PIPAAm Coated Nanofibers

As the coated nanofiber meshes were completed they were examined for surface topography, protein adsorption, and contact angle. Initially they were screened in house for uniformity by microscopic examination (looking for changes in pore size, and obvious delamination or uncoated areas) and for contact angles. Comparison between bulk PIPAAm, the coated and uncoated nanofiber mesh, and the hydrophobic polystyrene core will provide evidence for surface changes. Microscopic examination of the coated nanofibers showed no obvious delamination or changes in the morphology compared to the uncoated nanofibers.

Coatings which passed initial screening were assessed for protein adsorption. PIPAAm surfaces at 37° C. should adsorb considerably more protein than at 25° C. because of the phase transition. Coated and uncoated TCPS coverslips, incubated in 1×PBS buffer at 37° C. and 4° C. for two hours, then quickly removed and placed in a solution of 1 mg/ml BSA for 6 hours at 37° C. and 4° C. This time period should be enough for protein adsorption to occur. Following the BSA incubation, the pieces were rinsed three times with 1×PBS and placed in HRP-labeled anti-BSA antibody (Sigma) for 30 minutes, followed by a standard rinse and HRP colorimetric assay. Pieces were considered coated with the thermo-responsive polymer if the difference in protein adsorption between 37° C. and 25° C. incubated coated pieces exceeds one standard deviation and differs significantly from that of uncoated pieces.

Alternatively, we also adsorbed a cell adhesive protein, Fibronectin (FN). Bovine plasma FN (Biomedical Technology Inc, MA) was adsorbed onto the nanofibrillar surfaces by incubation of 10 μg/ml FN in PBS solution at 37° C. and 25° C. for 6 hours. The coated pieces were then vigorously washed with PBS for five times. They were blocked with 0.1% bovine serum albumin (BSA) in PBS for one hour and reacted with 2.0 mg/ml rabbit polyclonal anti bovine FN antibody (Biogenesis, Inc, UK) at a 1:200 dilution (final concentration, 10 μg/ml) for 2 hours at 37° C. and 25° C. respectively. Following five washes with PBS, containing 0.1% BSA, they were incubated for an additional one hour with anti rabbit IgG-HRP antibody (Chemicon International, CA) with a 1:1000 dilution (final concentration 15 μg/ml) and incubated with HRP substrate for 10 minutes. The color development was quenched with I.0N H2S04 and absorbance measurements were taken at 450 nm with a spectrophotometer (Spectramax M2).

A ten fold difference in protein adsorption was seen on PIPAAm coated surfaces incubated at 37° C. and 25° C. respectively. Surfaces that showed a difference in protein adsorption at 37° C. and 25° C. were further evaluated for their cell attachment and detachment profile by plating different cell lines.

Example 5

Cultured Bovine and Human Cells

Figure 5:
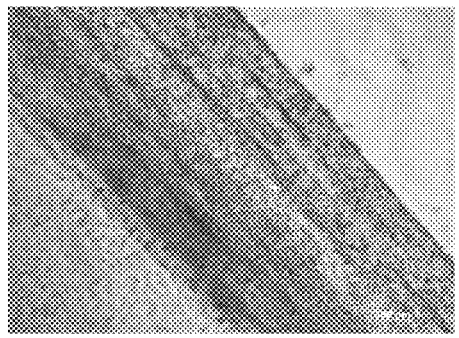
FIGS. 5 and 6 are electronic images of cell lift up times from various surfaces described in Example 5.
Figure 5:
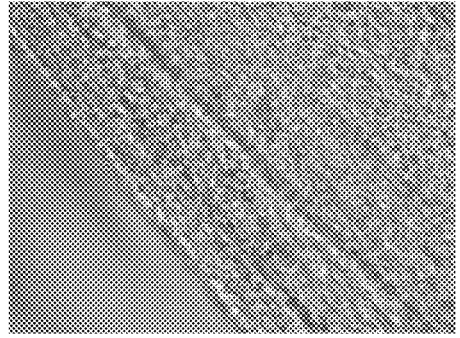
Figure 5:
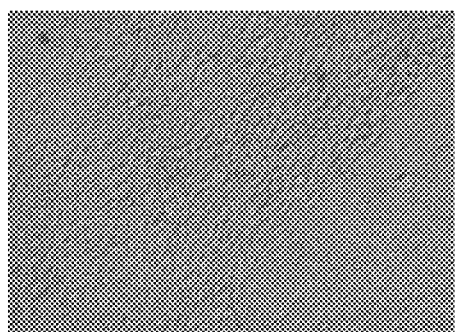
Figure 5:
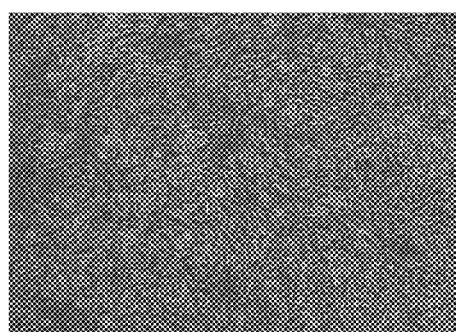
Figure 6:
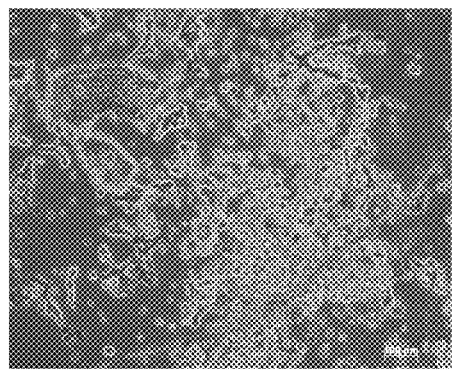
Figure 6:
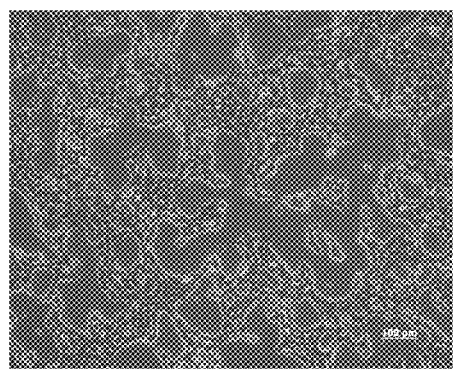
Figure 6:
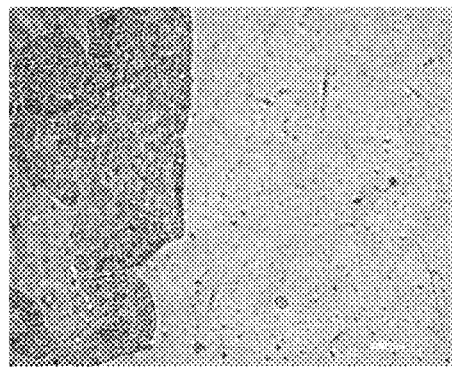
Figure 6:
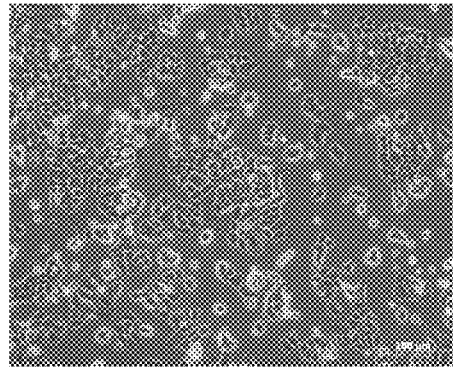

Bovine Aortic Endothelial Cells (BAEC) and T47-D cells were pre-cultured in 75 cm$^2$ flasks in DMEM-F12+10% FBS. The cells were trypsinized and plated on PIPAAm coated nanofibrillar and TCPS surfaces. The cells were also plated on commercially available PIPAAm coated TCPS surfaces Cell Seed Inc.). Both cell lines were plated at a density of 100,000 cells/well in 6-well PIPAAm coated dishes. Bare TCPS and Cell Seed surfaces were used as control surfaces and similar numbers of cells were plated on them. The cells were cultured for a period of 48 hours in a humidified atmosphere with 5% $CO_2$ at 37° C. Both the cell lines attached well to the coated surfaces which indicated that the coating was thin enough for the cells to attach. Forty eight hours later, the cells were moved to room temperature. The BAEC cells plated on PIPAAm coated nanofibers, TCPS and Cell Seed surfaces started to lift up in about 15-20 minutes. Approximately, after about 35 minutes complete cell sheets lifted up (FIG. 5). The results were more dramatic with T47-D cells. After 25 minutes incubation at room temperature, the cells began to sheet off from the PIPAAm/TriLite coated nanofibrillar and TCPS surfaces while the cells plated on Cell Seed surfaces failed to lift up even after 120 minutes of incubation at room temperature. It was observed that on Cell Seed surfaces, there was no cell detachment while 50-70% of the cells lifted up from PIPAAm/TriLite coated surfaces in about half the time (FIG. 6).

Example 6

Cultured Human Epithelial Cells

It has been shown that cells growing on nanofibrillar surfaces form more in vivo like morphologies. These surfaces are also permissive for epithelial cells to undergo morphogenesis. We have shown that our coating on smart polymer surfaces does not interfere with the nanofibrillar properties of the matrix and cells still undergo morphogenesis or form more in vivo like structures in addition to being detached by mere temperature reduction.

For morphogenesis studies, T47-D breast epithelial cells were cultured on nanofibrillar and flat surfaces coated with PIPAAm/TriLite. The controls were bare nanofibers and TCPS. The cells were cultured in DMEM+10% fetal bovine serum (FBS) in an atmosphere of 5% $CO_2$, 95% air at 37° C. This particular cell line has been selected as it has shown to demonstrate tubular and spheroidal structures under conditions that promote three dimensional interactions with collagen or matrigel. After, 10 days in culture, cells were fixed with 4% paraformaldehyde and incubated with Phalloidin Alexa Fluor 594 (1:500, Molecular Probes, OR) for 30 minutes at room temperature. The cells were rinsed three times with PBS and observed under an inverted fluorescent microscope (Zeiss Axiovert 200M). Phalloidin binds to filamentous actin (F-actin) and provides visualization of cytoskeletal organization of the cells. After 5 days in culture, a mixed population of spheroids and tubular cells was observed on nanofibers. By day 8, multicellular spheroids were dominant although some tubules still persisted. In contrast, the growth of T47-D cells on flat surfaces showed a monolayer with a group of stress fibers. We have shown that our coating on the nanofiber surface with the thermo-responsive polymer does not affect the nanofibrillar topology and hence morphogenesis of T47-D cells or more in vivo like cells can be obtained on these surfaces by mere reduction of temperature. To show that detached cells recover quickly on fresh surfaces and still retain their morphology after temperature reduction, the second set of cells was grown to confluency for about 5-10 days at 37° C. The cells were then moved to room temperature for about 15-40 minutes. The detached cell sheet was gently removed with the help of a 10.0 ml pipette to a fresh tissue culture surface. The cells were allowed to settle down and were then fixed with 4% paraformaldehyde after 30 minutes incubation at 37° C. Replated cells were stained with phalloidin F-actin to show that the advantage of growing cells on thermo-responsive nanofibrillar surfaces as opposed to flat thermo-responsive surfaces is the ability to achieve and retain in vivo like morphology (D).

Figure 7A:
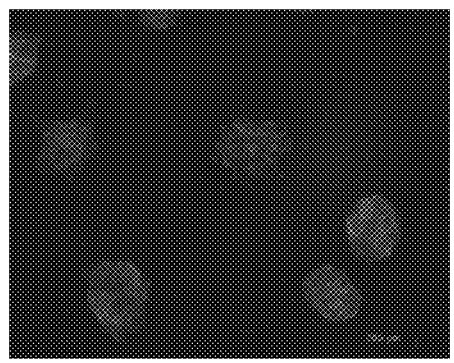
FIG. 7A shows multicellular spheroids on coated nanofibers.
Figure 7C:
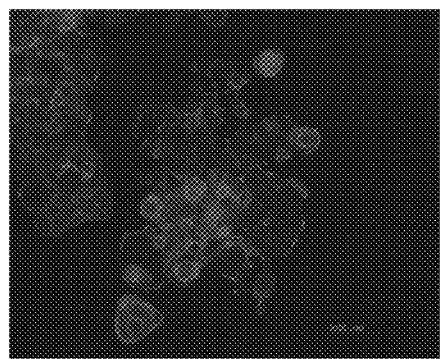
FIG. 7C shows spread out cellular morphology on coated TCPS.
Figure 7B:
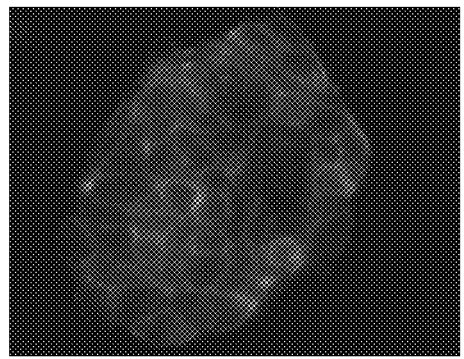
FIG. 7B is a magnified image of a spheroid shown in FIG. 7A.
Figure 7D:
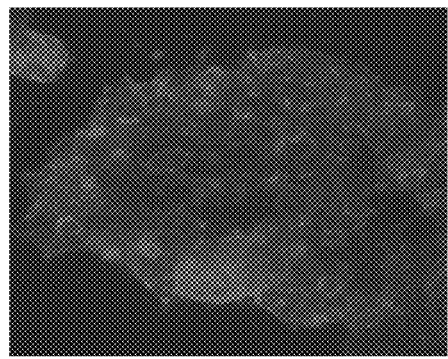
FIG. 7D shows cells lifted off and replated on nanofibers maintain morphology and peripheral organization.

FIG. 7A shows the T47-D cells cultured on PIPAAm/TriLite coated nanofibers for a period of 10 days and stained with Phalloidin F-actin. Note the presence of multicellular spheroids and the peripheral organization of actin filaments. A magnified image (400 μm) of the spheroid of FIG. 7B shows the lumen extending through the spheroid. T47-D cells cultured on PIPAAm/TriLite coated TCPS for period of 10 days were also fixed and stained for phalloidin F-actin. Note the spread out morphology and organization of stress fibers in the cells of FIG. 7C. T47-D cells lifted up through temperature reduction were replated on fresh nanofibers. FIG. 7D shows that replated T47-D cells maintain their tubular and spheroidal morphology and peripheral organization of actin (200 μm).

Figure 8:
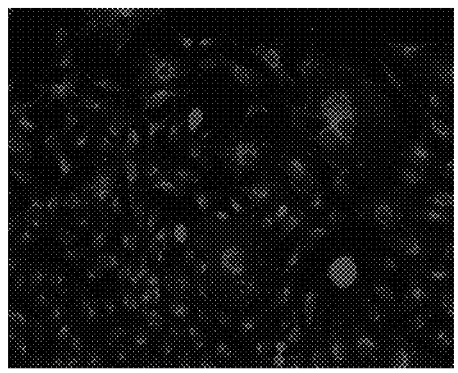
FIG. 8 is an electronic image of replated BAEC cells.
Figure 8:
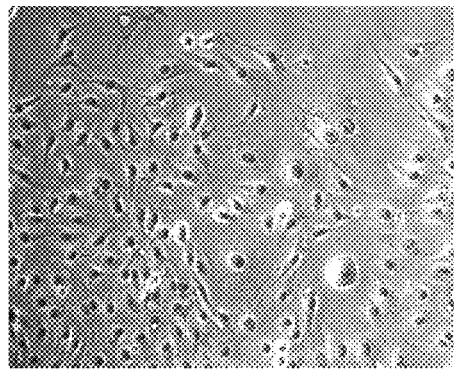

Replated cell sheets were also analyzed for conexxin 43 expression which is considered to be a major component of gap junctional channel. BAEC cells were plated at a density of 50,000 cells/22 mm well. The cells were cultured until confluency and then lifted up by moving the dish to 20° C. for 15 minutes. The sheets were transferred onto fresh nanofibrillar surfaces with the help of a 10 ml pipette and the curled up edges were uncurled by adding a drop of medium onto the sheet. The sheet was then transferred to the 5% CO2 humidified incubator at 37° C. and were allowed to attach. Thirty minutes later the cells were fixed with 4% paraformaldehyde and stained with 1:1000 dilution of anti connexin 43 (Sigma). Staining for Connexin 43 showed diffused expression of connexin 43 through out the entire sheet suggesting the presence of intact gap junctions (FIG. 8).

The invention claimed is:
1. A method for preparing a cell culture article, the method comprising steps of:
   (a) contacting a surface of the cell culture article with a coating composition, the coating composition comprising (i) a thermally responsive polymer that comprises poly(isopropylacrylamide), and (ii) a crosslinking agent having at least two latent reactive groups, wherein the cross linking agent is a compound of formula:

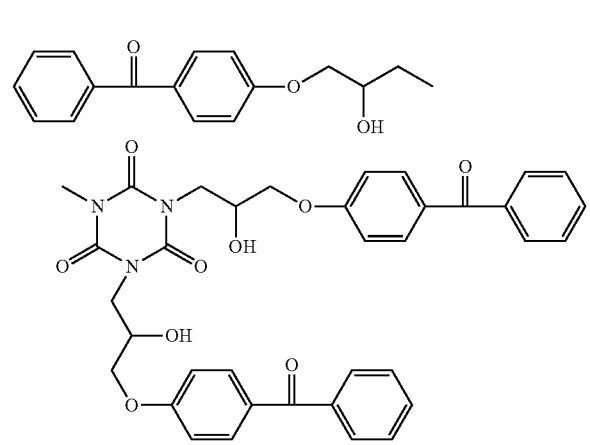

and (b) treating the coating composition to activate latent reactive groups of the crosslinking agent, thereby coupling the thermally responsive polymer to the surface of the cell culture article in a manner in which at least some of the latent reactive groups remain in an inactive state.

2. The method according to claim 1 further comprising a step of coupling a biologically active material to the surface of the cell culture device by activating remaining latent reactive groups of step (b).

3. The method according to claim 1 wherein the cell culture article comprises a nanofiber or nanofiber mesh.

4. The method according to claim 1 wherein the cell culture article is selected from slides, multi-well plates, Petri dishes, tissue culture plates, tissue culture flasks, and coverslips.

5. The method according to claim 1 wherein the step of contacting a surface of the cell culture article with a coating composition comprises contacting a surface of the cell culture article with the thermally responsive polymer, the crosslinking agent and a biologically active material.

6. The method according to claim 2 wherein the biologically active material is selected from enzymes, proteins, carbohydrates, nucleic acids, cells and mixtures of any two or more of these.

7. The method according to claim 5 wherein the biologically active material is selected from enzymes, proteins, carbohydrates, nucleic acids, cells and mixtures of any two or more of these.

8. A cell culture article prepared by the method of claim 1.

* * * * *